United States Patent [19]
Han et al.

[11] Patent Number: 5,837,810
[45] Date of Patent: Nov. 17, 1998

[54] POLYPEPTIDES OF LIPOPOLYSACCHARIDE BINDING PROTEIN

[75] Inventors: Jiahuai Han, La Jolla; Richard J. Ulevitch, Del Mar; Peter S. Tobias, San Diego, all of Calif.

[73] Assignee: The Scripps Research Institute, La Jolla, Calif.

[21] Appl. No.: 215,089

[22] Filed: Mar. 15, 1994

[51] Int. Cl.⁶ .................................................. C07K 14/47
[52] U.S. Cl. ............................................................ 530/350
[58] Field of Search .............................................. 530/350

[56] References Cited

U.S. PATENT DOCUMENTS 5,245,013   9/1993   Ulevitch .

OTHER PUBLICATIONS

Schuman, Science 249: 1429–1431, 1990.
Ooi, J. Exp Med 174: 649–655, 1991.

*Primary Examiner*—Paula K. Hutzell
*Assistant Examiner*—Nancy A. Johnson
*Attorney, Agent, or Firm*—Fish & Richardson, P.C.

[57] ABSTRACT

The present invention provides a first polypeptide fragment of lipopolysaccharide (LPS) binding protein (LBP) which binds to lipopolysaccharide, but prevents the LPS:LBP complex from either transferring LPS to CD14 or promoting the formation of an LPS:CD14 complex and a second polypeptide fragment of LBP which binds to CD14 receptor to inhibit binding of LPS:LBP complex to the CD14 receptor. Also included are methods of ameliorating symptoms of sepsis in a subject by administration of a LBP polypeptide of the invention, or administration of antibody to LBP polypeptide or anti-idiotype antibody.

1 Claim, 10 Drawing Sheets

```
ATG GGG GCC TTG GCA AGA GCC CTG CCG TCC ATA CTG CTG GCA TTG CTG        48
Met Gly Ala Leu Ala Arg Ala Leu Pro Ser Ile Leu Leu Ala Leu Leu
 1               5                  10                  15

CTT ACG TCC ACC CCA GAG GCT CTG GGT GCC AAC CCC GGC TTG GTC GCC        96
Leu Thr Ser Thr Pro Glu Ala Leu Gly Ala Asn Pro Gly Leu Val Ala
             20                  25                  30

AGG ATC ACC GAC AAG GGA CTG CAG TAT GCG GCC CAG GAG GGG CTA TTG       144
Arg Ile Thr Asp Lys Gly Leu Gln Tyr Ala Ala Gln Glu Gly Leu Leu
         35                  40                  45

GCT CTG CAG AGT GAG CTG CTC AGG ATC ACG CTG CCT GAC TTC ACC GGG       192
Ala Leu Gln Ser Glu Leu Leu Arg Ile Thr Leu Pro Asp Phe Thr Gly
     50                  55                  60

GAC TTG AGG ATC CCC CAC GTC GGC CGT GGG CGC TAT GAG TTC CAC AGC       240
Asp Leu Arg Ile Pro His Val Gly Arg Gly Arg Tyr Glu Phe His Ser
 65                  70                  75                  80

CTG AAC ATC CAC AGC TGT GAG CTG CTT CAC TCT GCG CTG AGG CCT GTC       288
Leu Asn Ile His Ser Cys Glu Leu Leu His Ser Ala Leu Arg Pro Val
                 85                  90                  95

CCC GGC CAG GGC CTG AGT CTC AGC ATC TCC GAC TCC TCC ATC CGG GTC       336
Pro Gly Gln Gly Leu Ser Leu Ser Ile Ser Asp Ser Ser Ile Arg Val
             100                 105                 110

CAG GGC AGG TGG AAG GTG CGC AAG TCA TTC TTC AAA CTA CAG GGC TCC       384
Gln Gly Arg Trp Lys Val Arg Lys Ser Phe Phe Lys Leu Gln Gly Ser
         115                 120                 125

TTT GAT GTC AGT GTC AAG GGC ATC AGC ATT TCG GTC AAC CTC CTG TTG       432
Phe Asp Val Ser Val Lys Gly Ile Ser Ile Ser Val Asn Leu Leu Leu
     130                 135                 140

GGC AGC GAG TCC TCC GGG AGG CCC ACA GGT TAC TGC CTC AGC TGC AGC       480
Gly Ser Glu Ser Ser Gly Arg Pro Thr Gly Tyr Cys Leu Ser Cys Ser
145                 150                 155                 160

AGT GAC ATC GCT GAC GTG GAG GTG GAC ATG TCG GGA GAT TCG GGG TGG       528
Ser Asp Ile Ala Asp Val Glu Val Asp Met Ser Gly Asp Ser Gly Trp
                 165                 170                 175

CTC TTG AAC CTC TTC CAC AAC CAG ATT GAG TCC AAG TTC CAG AAA GTA       576
Leu Leu Asn Leu Phe His Asn Gln Ile Glu Ser Lys Phe Gln Lys Val
             180                 185                 190

CTG GAG AGC AGG ATT TGC GAA ATG ATC CAG AAA TCA GTG TCC TCC GAT       624
Leu Glu Ser Arg Ile Cys Glu Met Ile Gln Lys Ser Val Ser Ser Asp
         195                 200                 205
```

FIG. 5A

```
CTA CAG CCT TAT CTC CAA ACT CTG CCA GTT ACA ACA GAG ATT GAC AGT    672
Leu Gln Pro Tyr Leu Gln Thr Leu Pro Val Thr Thr Glu Ile Asp Ser
    210             215                 220

TTC GCC GAC ATT GAT TAT AGC TTA GTG GAA GCC CCT CGG GCA ACA GCC    720
Phe Ala Asp Ile Asp Tyr Ser Leu Val Glu Ala Pro Arg Ala Thr Ala
225             230                 235                 240

CAG ATG CTG GAG GTG ATG TTT AAG GGT GAA ATC TTT CAT CGT AAC CAC    768
Gln Met Leu Glu Val Met Phe Lys Gly Glu Ile Phe His Arg Asn His
                245                 250                 255

CGT TCT CCA GTT ACC CTC CTT GCT GCA GTC ATG AGC CTT CCT GAG GAA    816
Arg Ser Pro Val Thr Leu Leu Ala Ala Val Met Ser Leu Pro Glu Glu
            260                 265                 270

CAC AAC AAA ATG GTC TAC TTT GCC ATC TCG GAT TAT GTC TTC AAC ACG    864
His Asn Lys Met Val Tyr Phe Ala Ile Ser Asp Tyr Val Phe Asn Thr
        275                 280                 285

GCC AGC CTG GTT TAT CAT GAG GAA GGA TAT CTG AAC TTC TCC ATC ACA    912
Ala Ser Leu Val Tyr His Glu Glu Gly Tyr Leu Asn Phe Ser Ile Thr
    290                 295                 300

GAT GAC ATG ATA CCG CCT GAC TCT AAT ATC CGA CTG ACC ACC AAG TCC    960
Asp Asp Met Ile Pro Pro Asp Ser Asn Ile Arg Leu Thr Thr Lys Ser
305             310                 315                 320

TTC CGA CCC TTC GTC CCA CGG TTA GCC AGG CTC TAC CCC AAC ATG AAC   1008
Phe Arg Pro Phe Val Pro Arg Leu Ala Arg Leu Tyr Pro Asn Met Asn
            325                 330                 335

CTG GAA CTC CAG GGA TCA GTG CCC TCT GCT CCG CTC CTG AAC TTC AGC   1056
Leu Glu Leu Gln Gly Ser Val Pro Ser Ala Pro Leu Leu Asn Phe Ser
                340                 345                 350

CCT GGG AAT CTG TCT GTG GAC CCC TAT ATG GAG ATA GAT GCC TTT GTG   1104
Pro Gly Asn Leu Ser Val Asp Pro Tyr Met Glu Ile Asp Ala Phe Val
            355                 360                 365

CTC CTG CCC AGC TCC AGC AAG GAG CCT GTC TTC CGG CTC AGT GTG GCC   1152
Leu Leu Pro Ser Ser Ser Lys Glu Pro Val Phe Arg Leu Ser Val Ala
    370                 375                 380

ACT AAT GTG TCC GCC ACC TTG ACC TTC AAT ACC AGC AAG ATC ACT GGG   1200
Thr Asn Val Ser Ala Thr Leu Thr Phe Asn Thr Ser Lys Ile Thr Gly
385             390                 395                 400

TTC CTG AAG CCA GGA AAG GTA AAA GTG GAA CTG AAA GAA TCC AAA GTT   1248
Phe Leu Lys Pro Gly Lys Val Lys Val Glu Leu Lys Glu Ser Lys Val
            405                 410                 415
```

FIG. 5B

```
GGA CTA TTC AAT GCA GAG CTG TTG GAA GCG CTC CTC AAC TAT TAC ATC    1296
Gly Leu Phe Asn Ala Glu Leu Leu Glu Ala Leu Leu Asn Tyr Tyr Ile
            420                 425                 430

CTT AAC ACC CTC TAC CCC AAG TTC AAT GAT AAG TTG GCC GAA GGC TTC    1344
Leu Asn Thr Leu Tyr Pro Lys Phe Asn Asp Lys Leu Ala Glu Gly Phe
            435                 440                 445

CCC CTT CCT CTG CTG AAG CGT GTT CAG CTC TAC GAC CTT GGG CTG CAG    1392
Pro Leu Pro Leu Leu Lys Arg Val Gln Leu Tyr Asp Leu Gly Leu Gln
        450                 455                 460

ATC CAT AAG GAC TTC CTG TTC TTG GGT GCC AAT GTC CAA TAC ATG AGA    1440
Ile His Lys Asp Phe Leu Phe Leu Gly Ala Asn Val Gln Tyr Met Arg
465                 470                 475                 480

GTT TGAGGACAAG AAAGATGAAG CTTGGAGGTC ACAGGCTGGA TCTGCTTGTT         1493
Val

GCATTTCCAG CTGTGCAGCA CGTCTCAGAG ATTCTTGAAG AATGAAGACA TTTCTGCTCT  1553

CAGCTCCGGG GGTGAGGTGT GCCTGGCCTC TGCCTCCACC CTCCTCCTCT TCACCAGGTG  1613

CATGCATGCC CTCTCTGAGT CTGGACTTTG CTTCCCCTCC AGGAGGGACC ACCCTCCCCG  1673

ACTGGCCTGG GATATCTTTA CAAGCAGGCA CTGTATTTTT TTATTCGCCA TCTGATCCCC  1733

ATGCCTAGCA GAGTGCTGGC ACTTAGTAGG TCCTCAATAA ATATTTAGGT CGACGAGCTC  1793

GAGAATTC                                                          1801
```

FIG. 5C

```
CTCCTGGCCC ACTGCACTGG GAATCTAGG ATG GGG GCC TTG GCA AGA GCC CTG      53
                                Met Gly Ala Leu Ala Arg Ala Leu
                                 1               5

CCG TCC ATA CTC CTC GCA TTG CTG CTT ACC TCC ACC CCA GAG GCT CTC     101
Pro Ser Ile Leu Leu Ala Leu Leu Leu Thr Ser Thr Pro Glu Ala Leu
        10              15                  20

GGT GCC AAC CCC GGC TTG GTC GCC AGG ATC ACC GAC AAG GGA CTG CAG     149
Gly Ala Asn Pro Gly Leu Val Ala Arg Ile Thr Asp Lys Gly Leu Gln
 25              30                  35                      40

TAT GCG GCC CAG GAG GGG CTA TTG GCT CTG CAG AGT GAG CTG CTC AGG     197
Tyr Ala Ala Gln Glu Gly Leu Leu Ala Leu Gln Ser Glu Leu Leu Arg
             45                  50                      55

ATC ACG CTG CCT GAC TTC ACC GGG GAC TTG AGG ATC CCC CAC GTC GGC     245
Ile Thr Leu Pro Asp Phe Thr Gly Asp Leu Arg Ile Pro His Val Gly
                 60                  65                  70

CGT GGG CGC TAT GAG TTC CAC AGC CTG AAC ATC CAC AGC TGT GAG CTG     293
Arg Gly Arg Tyr Glu Phe His Ser Leu Asn Ile His Ser Cys Glu Leu
             75                  80                  85

CTT CAC TCT GCG CTG AGG CCT GTC CCC GGC CAG GGC CTG AGT CTC AGC     341
Leu His Ser Ala Leu Arg Pro Val Pro Gly Gln Gly Leu Ser Leu Ser
         90                  95                 100

ATC TCC GAC TCC TCC ATC CGG GTC CAG GGC AGG TGG AAG GTC CGC AAG     389
Ile Ser Asp Ser Ser Ile Arg Val Gln Gly Arg Trp Lys Val Arg Lys
105                 110                 115                 120

TCA TTC TTC AAA CTA CAG GGC TCC TTT GAT GTC AGT GTC AAG GGC ATC     437
Ser Phe Phe Lys Leu Gln Gly Ser Phe Asp Val Ser Val Lys Gly Ile
                 125                 130                 135

AGC ATT TCG GTC AAC CTC CTG TTG GGC AGC GAG TCC TCC GGG AGG CCC     485
Ser Ile Ser Val Asn Leu Leu Leu Gly Ser Glu Ser Ser Gly Arg Pro
             140                 145                 150

ACA GGT TAC TGC CTC AGC TGC AGC AGT GAC ATC GCT GAC GTG GAG GTG     533
Thr Gly Tyr Cys Leu Ser Cys Ser Ser Asp Ile Ala Asp Val Glu Val
             155                 160                 165

GAC ATG TCC GGA GAT TCG GGG TGG CTG TTG AAC CTC TTC CAC AAC CAG     581
Asp Met Ser Gly Asp Ser Gly Trp Leu Leu Asn Leu Phe His Asn Gln
170                 175                 180

ATT GAG TCC AAG TTC CAG AAA GTA CTG GAG AGC AGG ATT                 620
Ile Glu Ser Lys Phe Gln Lys Val Leu Glu Ser Arg Ile
185                 190                 195
```

FIG. 6

```
TGC GAA ATG ATC CAG AAA TCA GTG TCC TCC GAT CTA CAG CCT TAT CTC    48
Cys Glu Met Ile Gln Lys Ser Val Ser Ser Asp Leu Gln Pro Tyr Leu
 1               5                  10                 15

CAA ACT CTG CCA GTT ACA ACA GAG ATT GAC AGT TTC GCC GAC ATT GAT    96
Gln Thr Leu Pro Val Thr Thr Glu Ile Asp Ser Phe Ala Asp Ile Asp
            20                  25                 30

TAT AGC TTA GTG GAA GCC CCT CGG GCA ACA GCC CAG ATG CTG GAG GTG   144
Tyr Ser Leu Val Glu Ala Pro Arg Ala Thr Ala Gln Met Leu Glu Val
        35                  40                  45

ATG TTT AAG GGT GAA ATC TTT CAT CGT AAC CAC CGT TCT CCA GTT ACC   192
Met Phe Lys Gly Glu Ile Phe His Arg Asn His Arg Ser Pro Val Thr
     50                  55                  60

CTC CTT GCT GCA GTC ATG AGC CTT CCT GAG GAA CAC AAC AAA ATG GTC   240
Leu Leu Ala Ala Val Met Ser Leu Pro Glu Glu His Asn Lys Met Val
 65                  70                  75                  80

TAC TTT GCC ATC TCG GAT TAT GTC TTC AAC ACG GCC AGC CTG GTT TAT   288
Tyr Phe Ala Ile Ser Asp Tyr Val Phe Asn Thr Ala Ser Leu Val Tyr
                 85                  90                  95

CAT GAG GAA GGA TAT CTG AAC TTC TCC ATC ACA GAT GAC ATG ATA CCG   336
His Glu Glu Gly Tyr Leu Asn Phe Ser Ile Thr Asp Asp Met Ile Pro
            100                 105                 110

CCT GAC TCT AAT ATC CGA CTG ACC ACC AAG TCC TTC CGA CCC TTC GTC   384
Pro Asp Ser Asn Ile Arg Leu Thr Thr Lys Ser Phe Arg Pro Phe Val
        115                 120                 125

CCA CGG TTA GCC AGG CTC TAC CCC AAC ATG AAC CTG GAA CTC CAG GGA   432
Pro Arg Leu Ala Arg Leu Tyr Pro Asn Met Asn Leu Glu Leu Gln Gly
130                 135                 140
```

FIG. 7A

```
TCA GTG CCC TCT GCT CCG CTC CTG AAC TTC AGC CCT GGG AAT CTG TCT      480
Ser Val Pro Ser Ala Pro Leu Leu Asn Phe Ser Pro Gly Asn Leu Ser
145             150                 155                 160

GTG GAC CCC TAT ATG GAG ATA GAT GCC TTT GTG CTC CTG CCC AGC TCC      528
Val Asp Pro Tyr Met Glu Ile Asp Ala Phe Val Leu Leu Pro Ser Ser
                165                 170                 175

AGC AAG GAG CCT GTC TTC CGG CTC AGT GTG GCC ACT AAT GTG TCC GCC      576
Ser Lys Glu Pro Val Phe Arg Leu Ser Val Ala Thr Asn Val Ser Ala
            180                 185                 190

ACC TTG ACC TTC AAT ACC AGC AAG ATC ACT GGG TTC CTG AAG CCA GGA      624
Thr Leu Thr Phe Asn Thr Ser Lys Ile Thr Gly Phe Leu Lys Pro Gly
        195                 200                 205

AAG GTA AAA GTG GAA CTG AAA GAA TCC AAA GTT GGA CTA TTC AAT GCA      672
Lys Val Lys Val Glu Leu Lys Glu Ser Lys Val Gly Leu Phe Asn Ala
    210                 215                 220

GAG CTG TTG GAA GCG CTC CTC AAC TAT TAC ATC CTT AAC ACC CTC TAC      720
Glu Leu Leu Glu Ala Leu Leu Asn Tyr Tyr Ile Leu Asn Thr Leu Tyr
225                 230                 235                 240

CCC AAG TTC AAT GAT AAG TTG GCC GAA GGC TTC CCC CTT CCT CTG CTG      768
Pro Lys Phe Asn Asp Lys Leu Ala Glu Gly Phe Pro Leu Pro Leu Leu
                245                 250                 255

AAG CGT GTT CAG CTC TAC GAC CTT GGG CTG CAG ATC CAT AAG GAC TTC      816
Lys Arg Val Gln Leu Tyr Asp Leu Gly Leu Gln Ile His Lys Asp Phe
            260                 265                 270

CTG TTC TTG GGT GCC AAT GTC CAA TAC ATG AGA GTT                      852
Leu Phe Leu Gly Ala Asn Val Gln Tyr Met Arg Val
        275                 280
```

FIG. 7B

POLYPEPTIDES OF LIPOPOLYSACCHARIDE BINDING PROTEIN

This invention was made with Government support under Grant No. Al 25563, Al 32021 and Al 15136 awarded by the National Institute of Health. The Government has certain rights in this invention.

BACKGROUND OF THE INVENTION

1. Field of the Invention

The present invention relates generally to polypeptides of lipopolysaccharide binding protein (LBP) that inhibit the binding of lipopolysaccharide (LPS) released by gram-negative bacteria to the CD14 receptor, and specifically to the use of these polypeptides to ameliorating sepsis and the symptoms of sepsis in a subject and for assaying for gram-negative bacterial LPS.

2. Description of Related Art

Sepsis is induced by a toxin, the introduction or accumulation of which is most commonly caused by infection or trauma. The initial symptoms of sepsis typically include chills, profuse sweat, irregularly remittent fever, prostration and the like, followed by persistant fever, hypotension leading to shock, neutropenia, leukopenia, disseminated intravascular coagulation, adult respiratory distress syndrome and multiple organ failure.

Sepsis-inducing toxins have been found associated with pathogenic bacteria, viruses, plants and venoms. Among the well described bacterial toxins are the endotoxins or lipopolysaccharides (LPS) of the gram-negative bacteria. These molecules are glycolipids that are ubiquitous in the outer membrane of all gram-negative bacteria. The gram-negative bacteria of the gastrointestinal tract produce disease by invasion of tissue and by release of pharmacologically active LPS from the cell wall. Endotoxins from a wide variety of unrelated species behave quite similarly, regardless of the inherent pathogenicity of the microorganism from which they are derived or their antigenic structure. In the intact microorganism, endotoxins exist as complexes of lipid, polysaccharide, glycolipid and non-covalently-bound protein. The biologic activity seems to be a property of a lipid and carbohydrate portion.

Septic shock is characterized by inadequate tissue perfusion, most frequently following gram-negative bacteremia. The most common causative organisms are *Escherichia coli*, Klebsiella-Enterobacter, Proteus, Pseudomonas, and Serratia. *Neisseria meningitidis* bacteremia and gram-negative anaerobic bacteremia with Bacteroides spp are also important causes of septic shock. Most of the bacteria which cause gram-negative sepsis are normal commensals in the gastrointestinal tract. From there they may spread to contiguous structures, as in peritonitis after appendiceal perforation, or they may migrate from the perineum into the urethra or bladder.

The primary response of the host to LPS involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes and endothelial cells. Each of these cell types are also capable of responding to LPS with an elaboration of potent inflammatory substances.

LPS is believed to be a primary cause of death in humans during gram-negative sepsis, particularly when the symptoms include adult respiratory distress syndrome (ARDS). One particular cytokine, tumor necrosis factor (TNF), has recently been reported to be a primary mediator of septic shock (Beutler, et al., *New Eng. J. Med.,* 316:379, 1987). Intravenous injection of LPS endotoxin from bacteria into experimental animals and man produces a rapid, transient release of TNF (Beutler, et al., *J. Immunol.,* 135:3972, 1985). Evidence that TNF is a critical mediator of septic shock comes primarily from experiments in which pretreatment of animals with anti-TNF antibodies reduces lethality (Beutler, et al., *Science,* 229:869, 1985; Mathison, et al., *J. Clin. Invest.* 81:1925, 1988). These reports suggest that inhibition of the secretion of TNF caused by LPS or other factors would ameliorate the often lethal symptoms of sepsis.

LPS binding protein (LBP) is a 58–60 kD serum glycoprotein which participates in the LPS-dependent activation of myeloid, endothelial, and epithelial cells. It does so by first binding to LPS to form a high affinity LPS:LBP complex (Schumann, et al., *Science,* 249:1429,1990; Tobias, et al, *Am. J. Respir. Cell. Mol. Biol.* 7:239, 1992). The complex then interacts with CD14 to form a LBP:LPS:CD14 complex. CD14 is present in vivo in two forms. Myeloid cells express a glycerophosphorylinositol-tailed, membrane-bound form of CD14 (mCD14). Binding of LPS to mCD14 is promoted by LBP and results in cell activation (Tobias, et al., *J. Immunol.* 150:3011, 1993; Ulevitch and Tobias, Curr. Opin. Immunol, 6:125, 1993). Additionally, a soluble form of CD14 without the glycerophosphorylinositol-tail (sCD14) circulates in the plasma. LBP also promotes the formation of LPS:sCD14 complexes. The LPS:sCD14 complexes then react with as yet unidentified receptors on epithelial cells resulting in cell activation (Frey, et al., *J. Exp. Med.,* 176:1665, 1992; Pugin, et al, *Proc. Natl. Acad. Sci. U.S.A.* 90:2744, 1993). Thus, it appears that LBP has at least two functions, formation of an LPS:LBP complex and promotion of the formation of an LPS:CD14 complex.

It is desirable to inhibit LPS:LBP:CD14 complex formation or inhibit the LPS:LBP complex from transferring LPS to CD14 to form an LPS:CD14 complex. The present invention provides polypeptides of LBP which bind to LPS, but prevents the LPS:LBP complex from promoting the formation of an LPS:CD14 complex and prevents LPS transfer to CD14 and also polypeptides of LBP which inhibit the binding of LPS:LBP complex to CD14.

SUMMARY OF THE INVENTION

The present invention is based on the unexpected discovery that a first specific region of the lipopolysaccharide (LPS) binding protein (LBP) is involved in binding to LPS, but lacks the ability to promote the formation of a LPS:LBP:-CD14 complex. Thus, the present invention provides a first polypeptide of LBP which, like native LBP, retains the ability to bind to LPS, but, unlike native LBP, does not have the ability to promote the formation of an LPS:CD14 complex.

The invention also provides a second specific region of LBP which, in contrast to the first polypeptides, does not bind to LPS, but binds to CD14. Thus, this second polypeptide of LBP can inhibit the interaction of LPS:LBP complex with CD14.

In the first embodiment of the invention, the amino acid sequence of the polypeptides of LBP is provided. Due to its ability to bind and form a complex with LPS, the first polypeptide of LBP is useful in an assay to detect LPS endotoxin in a sample.

The invention also provides a method of ameliorating sepsis or the symptoms of sepsis in a subject, comprising administering a therapeutically effective amount of polypeptide of LBP or antibody to the polypeptide of LBP. In addition, an antibiotic, anti-tumor necrosis factor (TNF) antibody or both, can be administered to the subject.

Finally, the invention provides a therapeutic composition comprising a polypeptide of LPS binding protein which inhibits the binding of an LPS:LBP complex to CD14.

BRIEF DESCRIPTION OF THE DRAWINGS

FIG. 5A, FIG. 5B, and FIG. 5C show the nucleotide and deduced amino acid sequence of human LBP (SEQ ID NO:8).

FIG. 6 shows the nucleotide and deduced amino acid sequence of amino acid residues 1–197 of human LBP (SEQ ID NO:1 and 2).

FIGS. 7A and FIG. 7B show the nucleotide and deduced amino acid sequence of amino acid residues 198–481 of human LBP (SEQ ID NO:6 and 7).

DETAILED DESCRIPTION OF THE INVENTION

Figure 1:
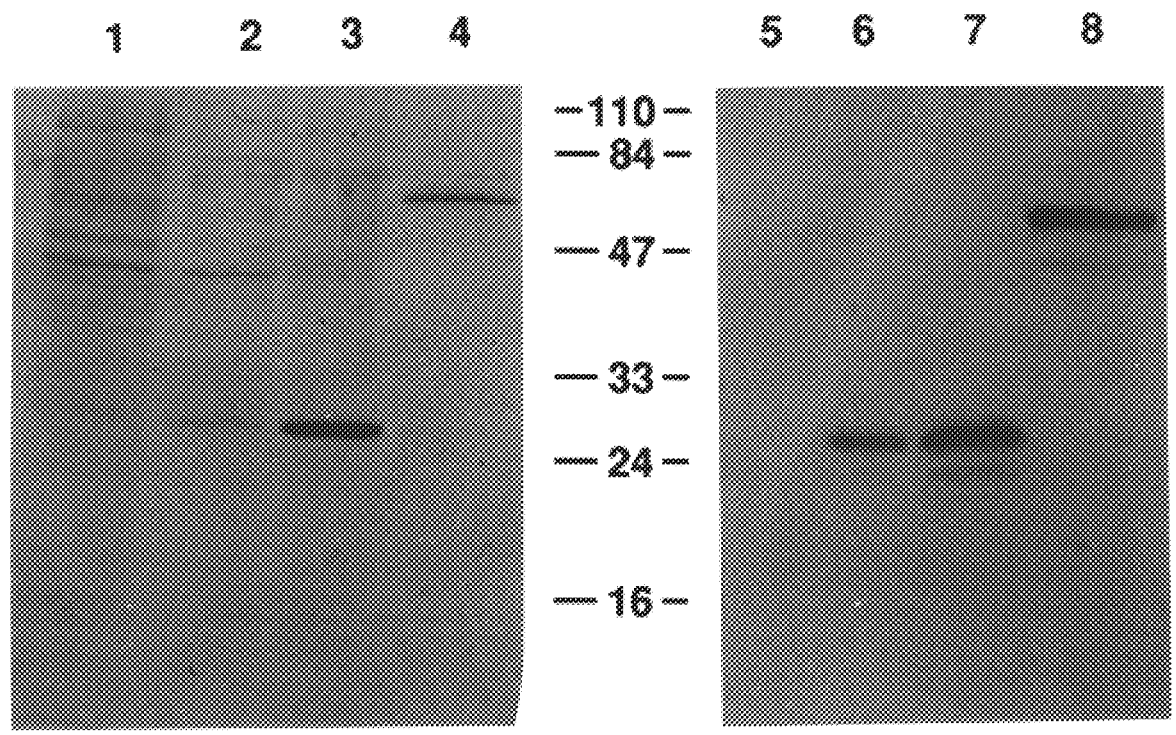
FIG. 1 shows an SDS-PAGE analysis of the purification of the amino terminal amino acids of LBP (NH-LBP). The left panel is a Coomassie-stained gel. The right panel shows a Western blot of an equivalent gel using polyclonal goat antiserum to human LBP. Lanes 1 and 5 show supernatant from untransfected cells; lanes 2 and 6 show supernatant from NH-LBP transfected cells; lanes 3 and 7 show NH-LBP partially purified by Bio-Rex 70 chromatography; and lanes 4 and 8 show human LBP.

The formation of a complex of lipopolysaccharide (LPS) and a full length lipopolysaccharide binding protein (LBP) polypeptide promotes the interaction of the LPS complex with either the soluble form of cell surface marker CD14 (sCD14) or membrane bound CD14 (mCD14). LPS:LBP complexes activate mononuclear blood cells by binding to the mCD14, triggering the production of cytokines for activation of endothelial cells. The present invention provides a "first polypeptide of LBP" or "first LBP polypeptide" which binds to LPS, but does not retain the ability to promote the association of a LPS with CD1 4, since the first polypeptide lacks that region of the LBP which has been now identified as being responsible for binding of the LPS:LBP complex to CD14. The polypeptide region of native or full-length LBP which is responsible for interaction with CD14 is noted herein as the "second polypeptide of LBP" or "second LBP polypeptide".

In a first embodiment, the invention provides an isolated first polypeptide of LBP with an amino acid sequence of SEQ ID NO:2, a second polypeptide with an amino acid sequence of SEQ ID NO:7 and functional fragments of the first and second polypeptides. The term "isolated" as used herein refers to polypeptide of LBP which is substantially free of other proteins, lipids, carbohydrates or other materials with which it is naturally associated. One skilled in the art can purify polypeptide of LBP using standard techniques for protein purification. The substantially pure first polypeptide will yield a single major band of about 27,000 daltons on a non-reducing polyacrylamide gel, whereas the second polypeptide has a single major band of about 31,000 daltons on a non-reducing polyacrylamide gel.

The first and second LBP polypeptide of the invention include "functional fragments" of the polypeptide, as long as the activity of the LBP polypeptide remains. Smaller peptides containing the biological activity of LBP polypeptides specifically exemplified herein are included in the invention.

The first LBP polypeptide of the invention refers to a polypeptide having the amino acid sequence of SEQ ID NO:2 and consists of amino terminal residues 1–197 of the native LBP. The present invention has identified the amino terminal region of LBP as having the LPS binding region, while the remaining carboxy terminal region (also noted herein as the second LBP polypeptide of the invention) is responsible for either transferring LPS to sCD1 4 or for forming a complex between LBP:LPS and CD14. Therefore, functional fragments of SEQ ID NO:2 include those amino terminal fragments which retain the ability to bind to LPS and which prevent LPS from associating with native LBP. An assay for determining whether a particular fragment of interest retains the functional activity of the polypeptide of SEQ ID NO:2 is described in Example 2 of the present application. Briefly, functional fragments of SEQ ID NO:7 include those carboxy terminal fragments which retain the ability to inhibit the transfer of LPS to sCD14 or to inhibit the interaction or association of LPS:LBP complex with CD14.

One of skill in the art is able to determine whether a particular fragment of interest has the functional activity of the polypeptide of the invention. For example, the assay outlined in Example 2 could be used to determine whether a polypeptide of interest has the ability to bind to LPS, but not CD14, or whether a polypeptide blocks LBP-LPS interaction. The ability of an amino terminal polypeptide of LBP to inhibit fluorescein-labeled LPS (FITC-LPS) binding to CD14 expressing cells can easily be assessed by FACS analysis. A second assay described in Example 2 utilizes a photoactivatable derivative of LPS which, upon photolysis, radioiodinates proteins to which it binds. Other labels and methods of assaying for functional equivalents of the polypeptides of the invention will be known to those of skill in the art.

The invention also provides polynucleotides encoding the LBP polypeptides of the invention. These polynucleotides include DNA, cDNA and RNA sequences which encode the LBP polypeptide. Therefore, the sequence as shown in SEQ ID NO:1 and 6, also includes those sequences where T (thymidine) is U (uracil) and nucleic acid sequences complementary to the sequence ID's shown herein. It is understood that all polynucleotides encoding all or a portion of LBP polypeptide are also included herein, as long as they encode a polypeptide with the activity of first LBP polypeptide or second LBP polypeptide, e.g., bind to LPS. Such polynucleotides include naturally occurring, synthetic, and intentionally manipulated polynucleotides. For example, LBP polypeptide polynucleotide may be subjected to site-directed mutagenesis. The polynucleotide sequence for LBP polypeptide also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of the LBP polypeptide encoded by the nucleotide sequence is functionally unchanged.

Minor modifications of the recombinant LBP polypeptide primary amino acid sequence may result in polypeptides which have substantially equivalent activity as compared to the first or second LBP polypeptides described herein. Such modifications may be deliberate, as by site-directed mutagenesis, or may be spontaneous. All of the polypeptides produced by these modifications are included herein as long as the biological activity of first or second LBP polypeptide still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which will not affect or are not required for LBP polypeptide biological activity.

The nucleotide sequence encoding the LBP polypeptides of the invention includes the disclosed sequences and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences and 2) antibody screening of expression libraries to detect cloned DNA fragments with shared structural features.

Preferably the LBP polypeptide polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the polypeptide in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res,* 9:879, 1981; Ausubel, et al,ed., *Current Protocols in Molecular Biology,* 1989).

The development of specific DNA sequences encoding LBP polypeptide of the invention can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. In addition, the LBP polypeptides of the invention can be obtained by polymerase chain reaction (PCR).

Of the above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for LBP polypeptide having at least one epitope, using antibodies specific for the LBP polypeptide. Such antibodies can be either polyclonally or mono-clonally derived and used to detect expression product indicative of the presence of LBP polypeptide cDNA.

DNA sequences encoding LBP polypeptide of the invention can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the LBP polypeptide polynucleotide sequences may be inserted into a recombinant expression vector. The term "recombinant expression vector" refers to a plasmid, virus or other vehicle known in the art that has been manipulated by insertion or incorporation of the LBP genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the PMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding LBP polypeptides of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or $RbCl_2$ can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the LBP polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies which bind to LBP polypeptides or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975). The term antibody as used in this invention is meant to include intact molecules as well as fragments thereof, such as Fab and F(ab')$_2$, which are capable of binding an epitopic determinant on LBP polypeptide. An antibody to LBP polypeptide of the invention would bind within the amino terminal sequence of first LBP polypeptide and prevent LPS from forming a complex with LBP or from forming a complex with CD14. Therefore, the antibody to first LBP polypeptide competitively inhibits the binding of LPS binding protein to LPS or LPS:LBP binding protein complex to CD14.

Likewise, antibody to the second LBP polypeptide of the invention would inhibit the binding of LPS:LBP complex to CD14 by blocking the interaction between the CD14 binding region of native LBP and CD14.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, in the present invention, an anti-idiotype antibody produced from an antibody which binds to a LBP polypeptide as in SEQ ID NO:2, or a synthetic peptide of SEQ ID NO:2, can act as a competitive inhibitor for a site on full length, native LBP which is required for binding to LPS, thereby preventing LPS from forming a complex with or being transferred to CD14 and thereby preventing activation of monocytes and other cells. Alternatively, an anti-idiotype antibody produced from an antibody which binds to an LBP polypeptide as in SEQ ID NO:7, or a synthetic peptide of SEQ ID NO:7 can act as a competitive inhibitor for a site on full length, native LBP which is required for binding of LPS:LBP complex with CD14.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier.

In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. A technique which may result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific antihapten antibodies. Those of skill in the art will know, or can readily discern, other immunoassay formats without undue experimentation.

The presence of LPS endotoxin secreted by gram-negative bacteria, for example, can be detected in vitro in a liquid body sample or other aqueous body sample that is suspected of containing LPS. Exemplary body samples include blood, serum, plasma, saliva, urine, and cerebrospinal fluid. Blood, serum and plasma are preferred body samples.

The body sample suspected of containing LPS is admixed with an LBP polypeptide as described to form an admixture. In the case of LBP first polypeptide, the admixture is maintained for an amount of time sufficient for the LBP polypeptide to react and form a complex with the LPS endotoxin present in the sample, for example about 10 minutes. It is well known in the art that the incubation time is a function of the amount of both the LBP and LPS in the admixture, with lower amounts typically requiring longer incubation times. Therefore, about 5 minutes to about 3 hours and preferably about 10 minutes to about 30 minutes is typical. The presence of the complex formed between the admixed first LBP polypeptide and LPS endotoxin is determined. The first LBP polypeptide is preferably labeled with a means for indicating the formation of the complex and the amount of complex formed.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Enzyme labels and their substrates include horseradish peroxidase and hydrogen peroxide and an oxidative dye precursor such as o-phenylenediamine and alkaline phosphatase typically used with p-nitrophenyl phosphate. Exemplary radioisotopes include $^3$H and $^{125}$I. Those of ordinary skill in the art will know of other suitable labels for binding to the antibody, or will be able to ascertain such, using routine experimentation.

Useful solid matrices which can be used in an in vitro detection method of the invention include such materials as cross-linked dextran (SEPHADEX), agarose, glass beads, nitrocellulose, or the wells of a microtiter plate such as those made from polystyrene or polyvinyl chloride.

In using a first LBP polypeptide of the invention for the in vivo detection of LPS, the detectably labeled LBP is given a dose which is diagnostically effective. The term "diagnostically effective" means that the amount of detectably labeled LBP polypeptide is administered in sufficient quantity to enable detection of the site having LPS.

In addition, a monoclonal antibody that binds to first or second LBP polypeptide could be used to detect LBP:LPS complexes in a subject.

The concentration of detectably labeled monoclonal antibody or first LBP polypeptide which is administered should be sufficient such that the binding to those cells having LPS or soluble LPS is detectable compared to the background. Further, it is desirable that the detectably labeled antibody or first LBP polypeptide be rapidly cleared from the circulatory system in order to give the best target-to-background signal ratio.

As a rule, the dosage of detectably labeled monoclonal antibody or first LBP polypeptide for in vivo diagnosis will vary depending on such factors as age, sex, and extent of disease of the individual. Such dosages may vary, for example, depending on whether multiple injections are given, LPS or antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to the antibody or first LBP polypeptide either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the antibodies or polypeptides of the invention are $^{111}$In, $^{97}$Ru, $^{67}$Ga, $^{68}$Ga, $^{72}$As, $^{89}$Zr, and $^{201}$Tl.

The first LBP polypeptide or antibody to first or second LBP polypeptide of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The invention provides a method of ameliorating sepsis or one or more of the symptoms of sepsis comprising administering to a subject displaying symptoms of sepsis or at risk for developing sepsis, a therapeutically effective amount of first or second LBP polypeptide or antibody that binds to first or second LBP polypeptide. Such symptoms which may be ameliorated include those associated with a transient increase in the blood level of TNF, such as fever, hypotension, neutropenia, leukopenia, thrombocytopenia, disseminated intravascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza* B, *Neisseria meningitides,* staphylococci, or pneumococci. Patients at risk for sepsis include those suffering from burns, gunshot wounds, renal or hepatic failure.

The term "therapeutically effective amount" as used herein refers to the amount of either first or second LBP polypeptide, antibody to first or second LBP polypeptide or anti-idiotype antibody which binds a paratope of an antibody which binds to the amino acid sequence of first or second LBP polypeptide, such as in SEQ ID NO:2 or SEQ ID NO:7, used in sufficient quantity to decrease the subject's response to LPS and decrease the symptoms of sepsis. The term "therapeutically effective" therefore includes that amount of first or second LBP polypeptide, antibody to first or second LBP polypeptide or anti-idiotype antibody to such antibody sufficient to prevent, and preferably reduce by at least 50%, and more preferably sufficient to reduce by 90%, a clinically significant increase in the plasma level of TNF. The dosage ranges for the administration of the first or second LBP polypeptide, antibody to first or second LBP polypeptide antibody, or anti-idiotype antibody to such antibody of the invention are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. An decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of a first or second LBP polypeptide, antibody to first or second LBP polypeptide, or anti-idiotype antibody to such antibody, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with an antibiotic in addition to the treatment with a first or second LBP polypeptide or antibody of the invention. Typical antibiotics include an aminoglycoside, such as gentamycin or a beta-lactam such as penicillin, or cephalosporin. Therefore, a preferred therapeutic method of the invention includes administering a therapeutically effective amount of first or second LBP polypeptide, antibody to first or second LBP polypeptide, or anti-idiotype antibody to such antibody, substantially simultaneously with administration of a bactericidal amount of an antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Preferably, administration of a first or second LBP polypeptide, or antibody to first or second LBP polypeptide, including anti-idiotype antibody of the invention, occurs within about 48 hours and preferably within about 2–8 hours, and most preferably, substantially concurrently with administration of the antibiotic.

The method of the invention also envisions treating the patient with a combination of the above described therapies. In other words, a patient may be administered in various combination, first or second LBP polypeptide, or antibody to first or second LBP polypeptide, including anti-idiotype antibody of the invention, an appropriate antibiotic, and an agent which decreases TNF in the patient, such as anti-TNF antibody.

In another embodiment, the invention provides a therapeutic composition which includes in a pharmaceutically acceptable carrier, one or more of a first or second LBP polypeptide, antibody which binds first or second LBP polypeptide, or anti-idiotype antibody which binds a paratope of an antibody which binds to the amino acid sequence of a first or second LBP polypeptide, such as in SEQ ID NO:2 or SEQ ID NO:7, respectively. As used herein, the term "pharmaceutically acceptable carrier" means a composition that is physiologically tolerable and does not typically cause an allergic or similar reaction, such as gastric upset or dizziness when administered to the subject.

Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient is often mixed with excipients which are pharmaceutically acceptable and compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

In addition, the therapeutic composition may further include an effective amount of one or more of the following active ingredients: at least one antibiotic, a steroid, an anti-TNF antibody and a TNF antagonist.

A polypeptide or antibody of the invention can be formulated into the therapeutic composition as neutralized pharmaceutically acceptable salt forms. These include the acid addition salts (formed with the free amino groups of the polypeptide or antibody molecule) and which are formed with inorganic acids such as, for example, hydrochloric or phosphoric acid, or organic acids such as acetic, oxalic, tartaric and the like. Salts also include those formed from inorganic bases such as, for example, sodium, potassium, ammonium, calcium or ferric hydroxides, and organic bases such as isopropylamine, trimethylamine, histidine, procaine and the like.

The following examples are intended to illustrate but not limit the invention. While they are typical of those that might be used, other procedures known to those skilled in the art may alternatively be used.

EXAMPLE 1

PRODUCTION OF LIPOPOLYSACCHARIDE (LPS) BINDING POLYPEPTIDE

The cDNA for the amino-terminal half of human LBP was generated from full-length human LBP cDNA (Schumann, et al., *Science*, 249:1429–1431, 1990) using polymerase chain reaction (PCR). Briefly, oligonucleotide primers with the sequences GTTCTAGACTGCACTGGGMTCTA (SEQ. ID NO:3) and AGGMTTCMATCTCTGTTGTMCTG (SEQ. ID NO:4) were used. DNA polymerase was used for 20 cycles (94° C., 55° C., and 72° C. for 1 min each) in an automated temperature cycler. The band corresponding to the half-molecule of LBP was purified by gel electrophoresis and ligated into the pEE14 vector (Bebbington and Hentschel, 1987) with XbaI and EcoRI sites. Analysis of the resultant DNA by restriction mapping (EcoRI, XbaI, BamHI, ClaI, and NarI) yielded fragments of the expected size.

CHO-K1 cells were transfected with this construct using calcium phosphate precipitation (Sambrook, et al., *Molecular Cloning*, pp. 16.01–16.81, 1989, Cold Spring Harbor Laboratory Press, Cold Spring Harbor, N.Y.). Cells expressing the truncated LBP, hereafter referred to as NH-LBP, were selected using methionine sulfoximine at 50 μm for 2 weeks, followed by increasing methionine sulfoximine to 200 μm for 2 months (Bebbington and Hentschel, *DNA Cloning*, Vol III, 163–188, 1987, IRL Press, Washington, D.C.).

Purification of NH-LBP was accomplished by ion exchange chromatography on Bio-Rex 70 and PL-Sax (in place of Mono Q) resins as described for human LBP (Schumann, et al., supra). The progress of the purification was monitored using Western blotting with polyclonal goat anti-human LBP as the detecting reagent followed by peroxidase-conjugated rabbit anti-goat IgG. The polyclonal goat anti-human LBP was prepared by immunization of a goat with human LBP expressed in an SF-9/baculovirus system (Summers and Smith, *A Manual of Methods for Baculovirus Vectors and Insect Cell Culture Procedures*, pp 1–57, 1988). A recombinant baculovirus containing the coding sequence for human LBP (Schumann, et al., supra) was used to infect the SF-9 cells. The expressed recombinant human LBP was purified as described above for NH-LBP.

Serum-free culture supernatants from CHO cells transfected with the NH-LBP construct showed evidence of NH-LBP expression by virtue of exhibiting an extra band in SDS-PAGE which stained positively with anti-human LBP IgG in Western blotting (FIG. 1). FIG. 1 shows an SDS-PAGE analysis of the purification of NH-LBP. The left panel is a Coomassie-stained gel. The right panel shows a Western blot of an equivalent gel using polyclonal goat antiserum to human LBP. Lanes 1 and 5 show supernatant from untransfected cells; lanes 2 and 6 show supernatant from NH-LBP transfected cells; lanes 3 and 7 show NH-LBP partially purified by Bio-Rex 70 chromatography; and lanes 4 and 8 show human LBP.

After isolation, using immunoreactivity with anti-human LBP in Western blotting to monitor the purification, the putative NH-LBP had an apparent molecular weight of 27,000 by SDS-PAGE, in reasonable agreement with the value of 21,660 calculated from the nucleic acid sequence of the cDNA. Amino-terminal microsequencing yielded ANPGL (SEQ ID NO:5) for the protein, in agreement with the amino-terminal sequence of human LBP. Finally, the cDNA construct yielded restriction fragments of the predicted size when digested with EcoRI, Xbal, BamHl, Clal, and Narl. Thus, the isolated expressed protein had the sequence deduced from the constructed cDNA, NH-LBP.

EXAMPLE 2

LBP POLYPEPTIDE BLOCKS LPS BINDING TO CD14

The ability of NH-LBP to promote or inhibit fluorescein-labeled LPS (FITC-LPS) binding to human CD14 expressing CHO cells (hCD14-CHO) was assessed by FACS analysis. FITC-LPS was prepared from *Salmonella Minnesota* Re595 LPS (Galanos, et al., *Eur. J. Biochem,* 9:245–249, 1969) and fluorescein isothiocyanate as described (Skelly, et al., *Infect. Immun.,* 23:287–293, 1979). hCD14-CHO cells (Kirkland, et al, *J. Biochem,* 268:24818–24823, 1993) (2×10$^5$/ml) were incubated with 5 ng/ml FITC-LPS for 30 min at 22° C. in Hank's balanced salt solution containing 0.3% bovine serum albumin before FACS analysis. Rabbit LBP (Tobias, et al., *J Exp. Med.* 164:77, 1986) or NH-LBP were added prior to addition of FITC-LPS. Quantitative estimation of the relative affinities of NH-LBP and LBP for FITC-LPS was accomplished as follows. From the definitions of the dissociation constants for LPS-NH-LBP and LPS-LBP complex formation and the fact that LPS is common to the two reactions one may write $K_{NH}$[LPS:NH-LBP]/[NH-LBP]=$K_{LBP}$[LPS:LBP]/[LBP]. When [LPS:NH-LBP]=[LPS:LBP], which occurs when NH-LBP inhibits 50% of the binding of FITC-LPS to hCD14-CHO cells, then $K_{NH}/K_{LBP}$ =[NH-LBP]/[LBP].

Direct evidence for the interaction of LPS with NH-LPS with NH-LBP was assessed with the use of $^{125}$I-ASD-LPS (ASD=2- (p-azidosalicylamido) ethyl-1,3'-dithiopropionate). $^{125}$I-ASD-LPS was prepared and photolyzed as previously described (Tobias, et al., supra, 1986). Aliquots of each reaction mixture were analyzed on 12% SDS-PAGE, revealing the $^{125}$I-labeled proteins by autoradiography. Labeled bands were identified by comparison of their mobilities with purified NH-LBP, LBP, or sCD14.

Figure 2:
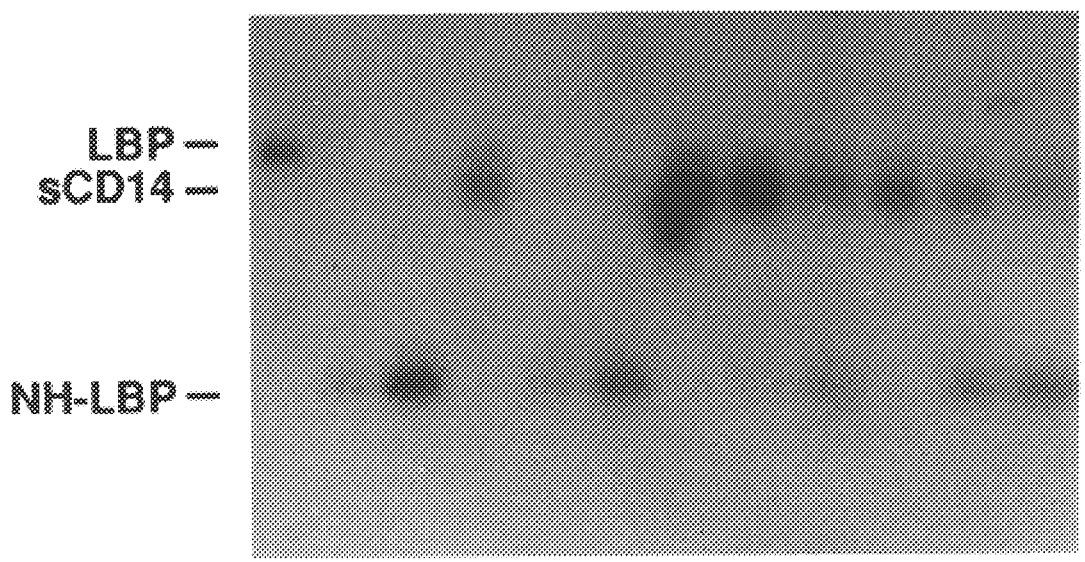
FIG. 2 shows a functional analysis of NH-LBP using $^{125}$I-ASD-LPS (2-(p-azidosalicylamido) ethyl-1,3'-dithiopropionate) labeling. Reaction mixtures contained LBP at $0.5 \times 10^{-8}$ M and/or sCD14 at $9 \times 10^{-8}$ M as indicated by (+). The concentrations of NH-LBP indicated in the figure are in units of $10^{-8}$ M. For lanes 1–9, all components were mixed with the $^{125}$I-ASD-LPS added last. For lanes 10–12, the $^{125}$I-ASD-LPS and NH-LBP were incubated for 10 min at room temperature before addition of the LBP and sCD14.

In a direct test of NH-LBP binding to LPS, NH-LBP was exposed to $^{125}$I-ASD-LPS, a photoactivatable derivative of LPS which, upon photolysis, radio-iodinates proteins to which it binds (Wollenweber and Morrison, *J Biol. Chem.,* 260:15068, 1985): FIG. 2 shows a functional analysis of NH-LBP using $^{125}$I-ASD-LPS labeling. Reaction mixtures contained LBP at 0.5×10$^{-8}$ M and/or sCD14 at 9×10$^{-8}$ M as indicated by (+). The concentrations of NH-LBP indicated in the figure are in units of 10$^{-8}$ M. For lanes 1–9, all components were mixed with the $^{125}$I-ASD-LPS added last. For lanes 10–12, the $^{125}$I-ASD- LPS and NH-LBP were incubated for 10 min at room temperature before addition of the LBP and sCD14. The complete reaction mixtures were incubated for 5 min at room temperature before photolysis for 2 min on ice.

When NH-LBP was incubated with $^{125}$I-ASD-LPS, photolyzed, and subjected to SDS-PAGE, the $^{125}$I band revealed by autoradiography had an apparent molecular weight of 27,000 and co-migrated with NH-LBP in the same gel as revealed by Coomasie Blue staining (FIG. 2, lanes 2 and 3). As shown in FIG. 2 (lane 1) and elsewhere (Schumann, et al., supra, 1990), LBP behaves similarly toward $^{125}$I-ASD-LPS. Thus, like LBP, NH-LBP is capable of binding $^{125}$I-ASD-LPS.

Although NH-LBP is capable of binding LPS, it is unable to promote the binding of LPS to either sCD14 or mCD14. Several different experiments shown in FIGS. 2 and 3 support this conclusion. When LBP and sCD14 are co-incubated with $^{125}$I-ASD-LPS for 5 min at room temperature, both the LBP and sCD14 become labeled (FIG. 2, lane 4), although in the absence of LBP, sCD14 is not labeled in this time period. However, in mixtures of NH-LBP and sCD14 with $^{125}$I-ASD-LPS, only NH-LBP becomes labeled, even when NH-LBP is present at 10 times the LBP concentration which leads to sCD14 labeling (FIG. 2, lanes 5 and 6). Thus, NH-LBP does not enable $^{125}$I-ASD-LPS to bind to sCD14.

Studies were also done to determine whether NH-LBP could successfully compete with LBP for $^{125}$I-ASD-LPS and inhibit labeling of sCD14. When NH-LBP and LBP were co-incubated with $^{125}$I-ASD-LPS before addition of LBP and sCD14, NH-LBP was able to inhibit $^{125}$I-ASD-LPS labeling of sCD14, as seen by comparing lanes 6–12 with lane 4 of FIG. 2. Preincubation of NH-LBP with $^{125}$I-ASD-LPS was more inhibitory than co-incubation of NH-LBP and LBP with $^{125}$I-ASD-LPS (compare FIG. 2, lanes 10–12 with 7–9). Judging by the slightly greater intensity of the radio-labeled NH-LBP than the radiolabeled LBP in lane 9 (FIG. 2), one might estimate that the affinity of NH-LBP for $^{125}$I-ASD-LPS is 50–100 fold less than the affinity of LBP for $^{125}$I-ASD-LPS. The affinity of LBP for Re595 LPS, used to prepare $^{125}$I-ASD-LPS, is estimated at $1\times10^{-9}$ M (Tobias, et al., *J. Bio. Chem.* 264:10867, 1989).

Figure 3A:
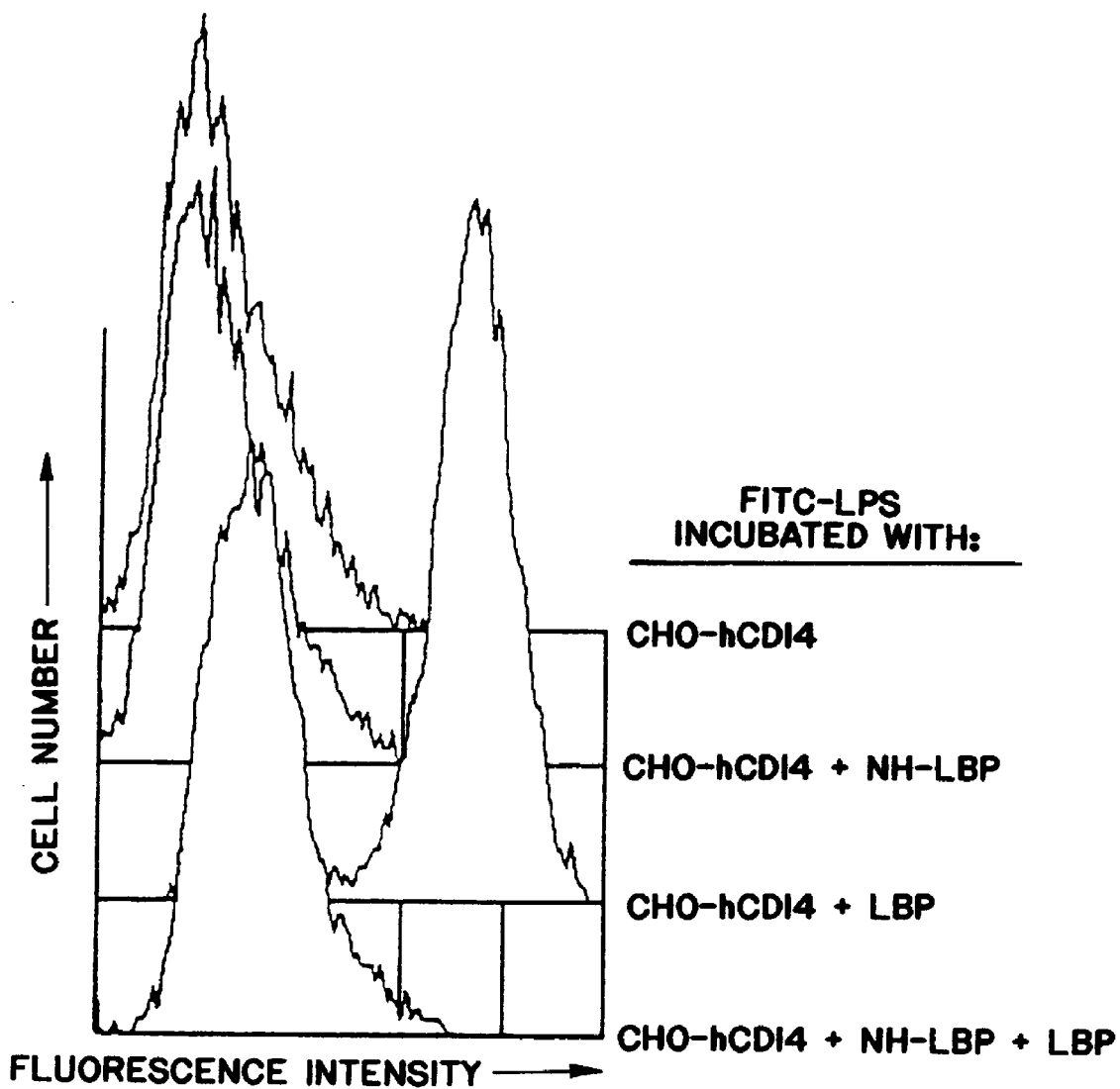
FIG. 3A shows FACS analysis of FITC-LPS binding to hCD14-CHO cells. 1, cells alone; 2, FITC-LPS plus NH-LBP with cells; 3, FITC-LPS plus LBP with cells; 4, FITC-LPS plus NH-LBP plus LBP with cells.
Figure 3B:
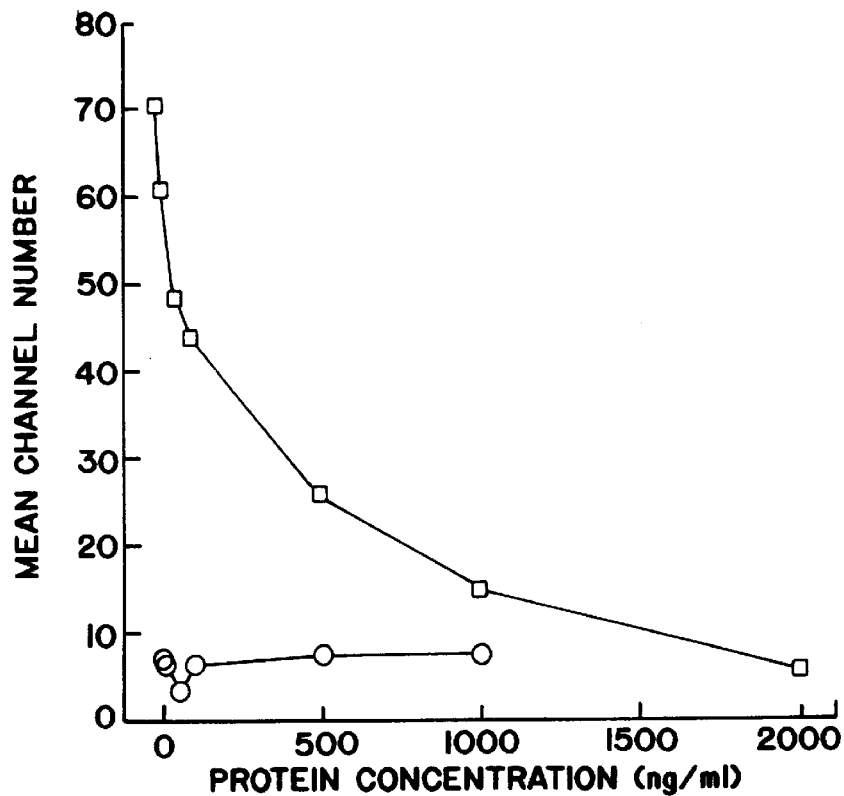
FIG. 3B shows inhibition of FITC-LPS binding to hCD14-CHO cells by NH-LBP. hCD14-CHO cells were mixed with FITC-LPS (5 ng/ml) in the presence of the indicated concentrations of NH-LBP with (□) or without (○) LBP (100 ng/ml).

The aforementioned properties of NH-LBP are not limited to $^{125}$I-ASD-LPS binding to sCD14 but can also be seen with membrane-bound CD14. CHO cells were transfected with a plasmid bearing the cDNA for human mCD1 4 and characterized the resulting cells (hCD1 4-CHO) as expressing a glycero-phosphorylinositol-bound form of human CD14 (Kirkland, et al, supra, 1993). The binding of [$^3$H]LPS to these cells has recently been described (Kirkland, et al., supra, 1993). FIG. 3 shows A, FACS analysis of FITC-LPS binding to hCD14-CHO cells. Peak 1 shows cells alone; 2, FITC-LPS plus NH-LBP with cells; 3, FITC-LPS plus LBP with cells; 4, FITC-LPS plus NH-LBP plus LBP with cells. FIG. 3B shows inhibition of FITC-LPS binding to hCD1 4-CHO cells by NH-LBP. hCD14-CHO cells were mixed with FITC-LPS (5 ng/ml) in the presence of the indicated concentrations of NH-LBP with (□) or without (○) LBP (100 ng/ml).

When incubated with FITC-LPS (FIG. 3A), the hCD14-CHO cells do not bind FITC-LPS unless LBP is added. In this regard, the hCD14-CHO cells display FITC-LPS binding that resembles the binding displayed by peripheral blood monocytes (Heumann, et al., *J. Immunol,* 148:3505–3512, 1992). Nh-LBP is unable to substitute for LBP and inhibits LBP-assisted FITC-LPS binding (FIG. 3A). The dose dependency of NH-LBP inhibition is shown in FIG. 3B. The binding of FITC-LPS to the cells enabled by 100 ng/ml LBP ($1.7\times109^{-9}$ M) is 50% inhibited by 250 ng/ml NH-LBP ($1.1\times10^{-8}$ M), suggesting that the dissociation constant of NH-LBP. LPS complexes is 6.4-fold larger (i.e., weaker binding) than the dissociation constant for LBP·LPS complexes, estimated to be $1\times10^{-9}$ M (Tobias, et al., 1989). The FACS measurement of FITC-LPS binding to hCD14-CHO cells is more quantitative than the densities of the auto-radiogram in FIG. 2, therefore one might give greater weight to this latter estimate of the relative affinities of LBP and NH-LBP for LPS. However, whichever estimate for the affinity of NH-LBP for LPS one accepts, the data suggest that the NH-LBP fragment must retain most of the LPS binding site.

EXAMPLE 3

ACTIVATION OF MACROPHAGES BY LBP POLYPEPTIDE

The effect of NH-LBP on macrophage activation was studied using rabbit peritoneal exudate macrophages (PEM). Mineral oil-elicited rabbit PEM were cultured in serum-free medium as described previously (Mathison, et al., *J. Clin. Invest,* 81:1925–1937, 1988). PEM were cultured in 96-well clusters (100–µl suspension containing $1\times10^5$ cells) for 2 h followed by washing to remove nonadherent cells and replenishment with 50 µl of serum-free medium. To minimize binding of LBP to the polystyrene wells, the culture medium was supplemented with 1% human serum albumin (Miles, Inc., Cutter Biological, Lot 88G04). NH-LBP (1 µg/ml final concentration) was added to macrophages followed immediately by native purified rabbit LBP (10 ng/ml final concentration) and 1 ng/ml 0111:B4 LPS. After 4 h at 37° C., 5% $CO_2$, conditioned medium was harvested for assay of tumor necrosis factor cytolytic activity using L929 cells (Mathison, et al., supra, 1988).

Figure 4:
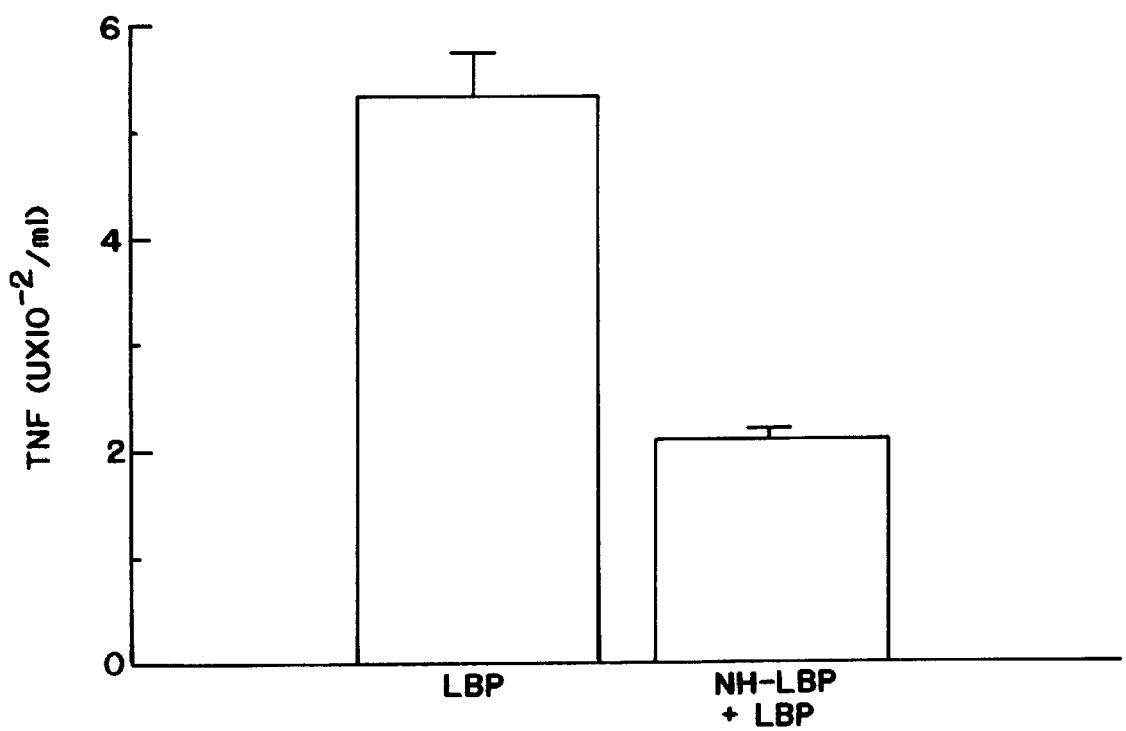
FIG. 4 shows the inhibition of LPS-initiated rabbit PEM activation by NH-LBP. Results are shown as TNF (Units/ml) for LBP and LBP+NH-LBP.

The aforementioned prompted an examination of the effects of NH-LBP on LPS-induced cell activation by the LBP/CD14-dependent pathway. To do this, the effect of NH-LBP on LPS-dependent activation of rabbit PEM to produce tumor necrosis factor was evaluated. FIG. 4 shows the inhibition of LPS-initiated rabbit PEM activation by NH-LBP. Results are shown as TNF (Units/ml) for LBP and LBP+NH-LBP.

As shown in FIG. 4, NH-LBP inhibited the LPS-and LBP-dependent activation of rabbit PEM.

FIGS. 5, 6 and 7 show the nucleotide and deduced amino acid sequence of human LBP, amino acid residues 1–197, and 198–481 of LBP, respectively.

The two functions of LBP, binding LPS and promoting the formation of LPS:CD14 complexes, are therefore, two distinct functions mediated by structurally distinct moieties of LBP. Clearly, the LPS binding function resides largely if not entirely within the NH-LBP fragment. In this regard, the closely related LPS binding proteins LBP and BPI resemble each other since the LPS binding site of BPI has been localized to sequences contained within a 23-kDa truncated form of BPI specifying residues 1–200 (Ooi, et al., *J. Exp. Med.,* 174:649–655, 1991). However, these studies shown in the Examples point out a marked difference between the functional domains of LBP and BPI since the 23-kDa form of BPI not only binds LPS but also defines the region of the molecule responsible for its antibacterial properties. Cholesteryl ester transfer protein, a protein that shows amino acid sequence similarities with both LBP and BPI (Schumann, et al., supra, 1990), also appears to have two distinct functional domains. However, the domains specifying the binding sites for cholesteryl esters and phospholipids (Swenson, et al, *J. Biol. Chem.* 263:5150, 1988) have not yet been associated with physically distinct entities.

The above disclosure generally describes the present invention. A more complete understanding can be obtained by reference to the following specific examples which are provided herein for purposes of illustration only and are not intended to limit the scope of the invention.

SUMMARY OF SEQUENCES

SEQ ID NO:1 is the nucleotide and deduced amino acid sequence for the first LBP polypeptide of the invention.

SEQ ID NO:2 is the deduced amino acid sequence for the first LBP polypeptide of the invention.

SEQ ID NO:3 and NO:4 are the nucleotide sequences for primers for PCR amplification of first LBP polypeptide.

SEQ ID NO:5 is the amino acid sequence of the residues 26–30 of the amino terminal amino acids of first LBP polypeptide.

SEQ ID NO:6 is the nucleotide and deduced amino acid sequence for the second LBP polypeptide of the invention.

SEQ ID NO:7 is the deduced amino acid sequence for the second LBP polypeptide of the invention.

SEQ ID NO:8 is the nucleotide sequence and deduced amino acid sequence for human LBP.

SEQ ID NO:9 is the deduced amino acid sequence for human LBP.

We claim:

1. An isolated polypeptide having the amino acid sequence of SEQ ID NO:2 and fragments thereof that bind LPS but do not form a complex with LPS and CD 14, or having the amino acid sequence of SEQ ID NO:7 and fragments thereof that bind with CD14 but do not form a complex with LPS and CD 14.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 620 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: N-terminal LBP ( i x ) FEATURE:
        ( A ) NAME/KEY: CDS
        ( B ) LOCATION: 30..620

( x i ) SEQUENCE DESCRIPTION: SEQ ID NO:1:

```
CTCCTGGCCC ACTGCACTGG GAATCTAGG ATG GGG GCC TTG GCA AGA GCC CTG         53
                                Met Gly Ala Leu Ala Arg Ala Leu
                                 1               5

CCG TCC ATA CTC CTC GCA TTG CTG CTT ACC TCC ACC CCA GAG GCT CTC        101
Pro Ser Ile Leu Leu Ala Leu Leu Leu Thr Ser Thr Pro Glu Ala Leu
     10              15                      20

GGT GCC AAC CCC GGC TTG GTC GCC AGG ATC ACC GAC AAG GGA CTG CAG        149
Gly Ala Asn Pro Gly Leu Val Ala Arg Ile Thr Asp Lys Gly Leu Gln
 25              30                      35                  40

TAT GCG GCC CAG GAG GGG CTA TTG GCT CTG CAG AGT GAG CTG CTC AGG        197
Tyr Ala Ala Gln Glu Gly Leu Leu Ala Leu Gln Ser Glu Leu Leu Arg
                 45              50                      55

ATC ACG CTG CCT GAC TTC ACC GGG GAC TTG AGG ATC CCC CAC GTC GGC        245
Ile Thr Leu Pro Asp Phe Thr Gly Asp Leu Arg Ile Pro His Val Gly
             60              65                      70

CGT GGG CGC TAT GAG TTC CAC AGC CTG AAC ATC CAC AGC TGT GAG CTG        293
Arg Gly Arg Tyr Glu Phe His Ser Leu Asn Ile His Ser Cys Glu Leu
         75              80                      85

CTT CAC TCT GCG CTG AGG CCT GTC CCC GGC CAG GGC CTG AGT CTC AGC        341
Leu His Ser Ala Leu Arg Pro Val Pro Gly Gln Gly Leu Ser Leu Ser
     90              95                     100

ATC TCC GAC TCC TCC ATC CGG GTC CAG GGC AGG TGG AAG GTC CGC AAG        389
Ile Ser Asp Ser Ser Ile Arg Val Gln Gly Arg Trp Lys Val Arg Lys
105             110                     115                 120

TCA TTC TTC AAA CTA CAG GGC TCC TTT GAT GTC AGT GTC AAG GGC ATC        437
Ser Phe Phe Lys Leu Gln Gly Ser Phe Asp Val Ser Val Lys Gly Ile
                 125                     130                 135

AGC ATT TCG GTC AAC CTC CTG TTG GGC AGC GAG TCC TCC GGG AGG CCC        485
Ser Ile Ser Val Asn Leu Leu Leu Gly Ser Glu Ser Ser Gly Arg Pro
             140                     145                 150

ACA GGT TAC TGC CTC AGC TGC AGC AGT GAC ATC GCT GAC GTG GAG GTG        533
Thr Gly Tyr Cys Leu Ser Cys Ser Ser Asp Ile Ala Asp Val Glu Val
         155                     160                 165

GAC ATG TCC GGA GAT TCG GGG TGG CTG TTG AAC CTC TTC CAC AAC CAG        581
Asp Met Ser Gly Asp Ser Gly Trp Leu Leu Asn Leu Phe His Asn Gln
     170                     175                 180

ATT GAG TCC AAG TTC CAG AAA GTA CTG GAG AGC AGG ATT                    620
Ile Glu Ser Lys Phe Gln Lys Val Leu Glu Ser Arg Ile
185                 190                     195
```

( 2 ) INFORMATION FOR SEQ ID NO:2:

( i ) SEQUENCE CHARACTERISTICS:
        ( A ) LENGTH: 197 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Ala Leu Ala Arg Ala Leu Pro Ser Ile Leu Leu Ala Leu Leu
 1               5                  10                  15
Leu Thr Ser Thr Pro Glu Ala Leu Gly Ala Asn Pro Gly Leu Val Ala
             20                  25                  30
Arg Ile Thr Asp Lys Gly Leu Gln Tyr Ala Ala Gln Glu Gly Leu Leu
         35                  40                  45
Ala Leu Gln Ser Glu Leu Leu Arg Ile Thr Leu Pro Asp Phe Thr Gly
     50                  55                  60
Asp Leu Arg Ile Pro His Val Gly Arg Gly Arg Tyr Glu Phe His Ser
 65                  70                  75                  80
Leu Asn Ile His Ser Cys Glu Leu Leu His Ser Ala Leu Arg Pro Val
                 85                  90                  95
Pro Gly Gln Gly Leu Ser Leu Ser Ile Ser Asp Ser Ser Ile Arg Val
             100                 105                 110
Gln Gly Arg Trp Lys Val Arg Lys Ser Phe Phe Lys Leu Gln Gly Ser
         115                 120                 125
Phe Asp Val Ser Val Lys Gly Ile Ser Ile Ser Val Asn Leu Leu Leu
     130                 135                 140
Gly Ser Glu Ser Ser Gly Arg Pro Thr Gly Tyr Cys Leu Ser Cys Ser
145                 150                 155                 160
Ser Asp Ile Ala Asp Val Glu Val Asp Met Ser Gly Asp Ser Gly Trp
                 165                 170                 175
Leu Leu Asn Leu Phe His Asn Gln Ile Glu Ser Lys Phe Gln Lys Val
                 180                 185                 190
Leu Glu Ser Arg Ile
             195
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..24

( x i ) SEQUENCE DESCRIPTION: SEQ ID NO:3:

```
GTTCTAGACT GCACTGGGAA TCTA                                    24
```

( 2 ) INFORMATION FOR SEQ ID NO:4:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

(ix) FEATURE:
    (A) NAME/KEY: CDS
    (B) LOCATION: 1..26

(xi) SEQUENCE DESCRIPTION: SEQ ID NO:4:

AGGAATTCAA ATCTCTGTTG TAACTG    26

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5

(xi) SEQUENCE DESCRIPTION: SEQ ID NO:5:

Ala  Asn  Pro  Gly  Leu
    1                    5

(2) INFORMATION FOR SEQ ID NO:6:

(i) SEQUENCE CHARACTERISTICS:
        (A) LENGTH: 852 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: C-terminal LBP (ix) FEATURE:
        (A) NAME/KEY: CDS
        (B) LOCATION: 1..852

(xi) SEQUENCE DESCRIPTION: SEQ ID NO:6:

```
TGC  GAA  ATG  ATC  CAG  AAA  TCA  GTG  TCC  TCC  GAT  CTA  CAG  CCT  TAT  CTC     48
Cys  Glu  Met  Ile  Gln  Lys  Ser  Val  Ser  Ser  Asp  Leu  Gln  Pro  Tyr  Leu
 1                   5                        10                      15

CAA  ACT  CTG  CCA  GTT  ACA  ACA  GAG  ATT  GAC  AGT  TTC  GCC  GAC  ATT  GAT     96
Gln  Thr  Leu  Pro  Val  Thr  Thr  Glu  Ile  Asp  Ser  Phe  Ala  Asp  Ile  Asp
                20                       25                      30

TAT  AGC  TTA  GTG  GAA  GCC  CCT  CGG  GCA  ACA  GCC  CAG  ATG  CTG  GAG  GTG    144
Tyr  Ser  Leu  Val  Glu  Ala  Pro  Arg  Ala  Thr  Ala  Gln  Met  Leu  Glu  Val
           35                      40                       45

ATG  TTT  AAG  GGT  GAA  ATC  TTT  CAT  CGT  AAC  CAC  CGT  TCT  CCA  GTT  ACC    192
Met  Phe  Lys  Gly  Glu  Ile  Phe  His  Arg  Asn  His  Arg  Ser  Pro  Val  Thr
      50                      55                       60

CTC  CTT  GCT  GCA  GTC  ATG  AGC  CTT  CCT  GAG  GAA  CAC  AAC  AAA  ATG  GTC    240
Leu  Leu  Ala  Ala  Val  Met  Ser  Leu  Pro  Glu  Glu  His  Asn  Lys  Met  Val
 65                       70                      75                       80

TAC  TTT  GCC  ATC  TCG  GAT  TAT  GTC  TTC  AAC  ACG  GCC  AGC  CTG  GTT  TAT    288
Tyr  Phe  Ala  Ile  Ser  Asp  Tyr  Val  Phe  Asn  Thr  Ala  Ser  Leu  Val  Tyr
                     85                      90                       95

CAT  GAG  GAA  GGA  TAT  CTG  AAC  TTC  TCC  ATC  ACA  GAT  GAC  ATG  ATA  CCG    336
His  Glu  Glu  Gly  Tyr  Leu  Asn  Phe  Ser  Ile  Thr  Asp  Asp  Met  Ile  Pro
               100                     105                      110

CCT  GAC  TCT  AAT  ATC  CGA  CTG  ACC  ACC  AAG  TCC  TTC  CGA  CCC  TTC  GTC    384
Pro  Asp  Ser  Asn  Ile  Arg  Leu  Thr  Thr  Lys  Ser  Phe  Arg  Pro  Phe  Val
          115                     120                      125
```

| | | | | | | | | | | | | | | | | |
|---|---|---|---|---|---|---|---|---|---|---|---|---|---|---|---|---|
|CCA|CGG|TTA|GCC|AGG|CTC|TAC|CCC|AAC|ATG|AAC|CTG|GAA|CTC|CAG|GGA|432|
|Pro|Arg|Leu|Ala|Arg|Leu|Tyr|Pro|Asn|Met|Asn|Leu|Glu|Leu|Gln|Gly| |
| |130| | | |135| | | |140| | | | | | | |
|TCA|GTG|CCC|TCT|GCT|CCG|CTC|CTG|AAC|TTC|AGC|CCT|GGG|AAT|CTG|TCT|480|
|Ser|Val|Pro|Ser|Ala|Pro|Leu|Leu|Asn|Phe|Ser|Pro|Gly|Asn|Leu|Ser| |
|145| | | | |150| | | |155| | | | | |160| |
|GTG|GAC|CCC|TAT|ATG|GAG|ATA|GAT|GCC|TTT|GTG|CTC|CTG|CCC|AGC|TCC|528|
|Val|Asp|Pro|Tyr|Met|Glu|Ile|Asp|Ala|Phe|Val|Leu|Leu|Pro|Ser|Ser| |
| | | | |165| | | | |170| | | | |175| | |
|AGC|AAG|GAG|CCT|GTC|TTC|CGG|CTC|AGT|GTG|GCC|ACT|AAT|GTG|TCC|GCC|576|
|Ser|Lys|Glu|Pro|Val|Phe|Arg|Leu|Ser|Val|Ala|Thr|Asn|Val|Ser|Ala| |
| | | |180| | | | |185| | | | |190| | | |
|ACC|TTG|ACC|TTC|AAT|ACC|AGC|AAG|ATC|ACT|GGG|TTC|CTG|AAG|CCA|GGA|624|
|Thr|Leu|Thr|Phe|Asn|Thr|Ser|Lys|Ile|Thr|Gly|Phe|Leu|Lys|Pro|Gly| |
| | |195| | | | |200| | | | |205| | | | |
|AAG|GTA|AAA|GTG|GAA|CTG|AAA|GAA|TCC|AAA|GTT|GGA|CTA|TTC|AAT|GCA|672|
|Lys|Val|Lys|Val|Glu|Leu|Lys|Glu|Ser|Lys|Val|Gly|Leu|Phe|Asn|Ala| |
| |210| | | |215| | | | |220| | | | | | |
|GAG|CTG|TTG|GAA|GCG|CTC|CTC|AAC|TAT|TAC|ATC|CTT|AAC|ACC|CTC|TAC|720|
|Glu|Leu|Leu|Glu|Ala|Leu|Leu|Asn|Tyr|Tyr|Ile|Leu|Asn|Thr|Leu|Tyr| |
|225| | | | |230| | | | |235| | | | |240| |
|CCC|AAG|TTC|AAT|GAT|AAG|TTG|GCC|GAA|GGC|TTC|CCC|CTT|CCT|CTG|CTG|768|
|Pro|Lys|Phe|Asn|Asp|Lys|Leu|Ala|Glu|Gly|Phe|Pro|Leu|Pro|Leu|Leu| |
| | | | |245| | | | |250| | | | |255| | |
|AAG|CGT|GTT|CAG|CTC|TAC|GAC|CTT|GGG|CTG|CAG|ATC|CAT|AAG|GAC|TTC|816|
|Lys|Arg|Val|Gln|Leu|Tyr|Asp|Leu|Gly|Leu|Gln|Ile|His|Lys|Asp|Phe| |
| | | |260| | | | |265| | | | |270| | | |
|CTG|TTC|TTG|GGT|GCC|AAT|GTC|CAA|TAC|ATG|AGA|GTT| | | | |852|
|Leu|Phe|Leu|Gly|Ala|Asn|Val|Gln|Tyr|Met|Arg|Val| | | | | |
| | |275| | | | |280| | | | | | | | | |

( 2 ) INFORMATION FOR SEQ ID NO:7:

( i ) SEQUENCE CHARACTERISTICS:
        ( A ) LENGTH: 284 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

| | | | | | | | | | | | | | | | |
|---|---|---|---|---|---|---|---|---|---|---|---|---|---|---|---|
|Cys|Glu|Met|Ile|Gln|Lys|Ser|Val|Ser|Ser|Asp|Leu|Gln|Pro|Tyr|Leu|
|1| | | |5| | | | |10| | | | |15| |
|Gln|Thr|Leu|Pro|Val|Thr|Thr|Glu|Ile|Asp|Ser|Phe|Ala|Asp|Ile|Asp|
| | | |20| | | | |25| | | | |30| | |
|Tyr|Ser|Leu|Val|Glu|Ala|Pro|Arg|Ala|Thr|Ala|Gln|Met|Leu|Glu|Val|
| | |35| | | | |40| | | | |45| | | |
|Met|Phe|Lys|Gly|Glu|Ile|Phe|His|Arg|Asn|His|Arg|Ser|Pro|Val|Thr|
| |50| | | | |55| | | | |60| | | | |
|Leu|Leu|Ala|Ala|Val|Met|Ser|Leu|Pro|Glu|Glu|His|Asn|Lys|Met|Val|
|65| | | | |70| | | | |75| | | | |80|
|Tyr|Phe|Ala|Ile|Ser|Asp|Tyr|Val|Phe|Asn|Thr|Ala|Ser|Leu|Val|Tyr|
| | | | |85| | | | |90| | | | |95| |
|His|Glu|Glu|Gly|Tyr|Leu|Asn|Phe|Ser|Ile|Thr|Asp|Asp|Met|Ile|Pro|
| | | |100| | | | |105| | | | |110| | |
|Pro|Asp|Ser|Asn|Ile|Arg|Leu|Thr|Thr|Lys|Ser|Phe|Arg|Pro|Phe|Val|
| | |115| | | | |120| | | | |125| | | |
|Pro|Arg|Leu|Ala|Arg|Leu|Tyr|Pro|Asn|Met|Asn|Leu|Glu|Leu|Gln|Gly|
| |130| | | | |135| | | | |140| | | | |
|Ser|Val|Pro|Ser|Ala|Pro|Leu|Leu|Asn|Phe|Ser|Pro|Gly|Asn|Leu|Ser|

-continued

| | | | | 145 | | | | 150 | | | | 155 | | | | 160 |
|---|---|---|---|---|---|---|---|---|---|---|---|---|---|---|---|---|
| Val | Asp | Pro | Tyr | Met 165 | Glu | Ile | Asp | Ala | Phe 170 | Val | Leu | Leu | Pro | Ser 175 | Ser |
| Ser | Lys | Glu | Pro 180 | Val | Phe | Arg | Leu | Ser 185 | Val | Ala | Thr | Asn | Val 190 | Ser | Ala |
| Thr | Leu | Thr 195 | Phe | Asn | Thr | Ser | Lys 200 | Ile | Thr | Gly | Phe | Leu 205 | Lys | Pro | Gly |
| Lys | Val 210 | Lys | Val | Glu | Leu | Lys 215 | Glu | Ser | Lys | Val | Gly 220 | Leu | Phe | Asn | Ala |
| Glu 225 | Leu | Leu | Glu | Ala | Leu 230 | Leu | Asn | Tyr | Tyr | Ile 235 | Leu | Asn | Thr | Leu | Tyr 240 |
| Pro | Lys | Phe | Asn | Asp 245 | Lys | Leu | Ala | Glu | Gly 250 | Phe | Pro | Leu | Pro | Leu 255 | Leu |
| Lys | Arg | Val | Gln 260 | Leu | Tyr | Asp | Leu | Gly 265 | Leu | Gln | Ile | His | Lys 270 | Asp | Phe |
| Leu | Phe | Leu 275 | Gly | Ala | Asn | Val | Gln 280 | Tyr | Met | Arg | Val | | | | |

( 2 ) INFORMATION FOR SEQ ID NO:8:

( i ) SEQUENCE CHARACTERISTICS:
        ( A ) LENGTH: 1801 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: human LBP ( i x ) FEATURE:
        ( A ) NAME/KEY: CDS
        ( B ) LOCATION: 1..1443

( x i ) SEQUENCE DESCRIPTION: SEQ ID NO:8:

| ATG | GGG | GCC | TTG | GCA | AGA | GCC | CTG | CCG | TCC | ATA | CTG | CTG | GCA | TTG | CTG | 48 |
|---|---|---|---|---|---|---|---|---|---|---|---|---|---|---|---|---|
| Met 1 | Gly | Ala | Leu | Ala 5 | Arg | Ala | Leu | Pro | Ser 10 | Ile | Leu | Leu | Ala | Leu 15 | Leu | |
| CTT | ACG | TCC | ACC | CCA | GAG | GCT | CTG | GGT | GCC | AAC | CCC | GGC | TTG | GTC | GCC | 96 |
| Leu | Thr | Ser | Thr 20 | Pro | Glu | Ala | Leu | Gly 25 | Ala | Asn | Pro | Gly | Leu 30 | Val | Ala | |
| AGG | ATC | ACC | GAC | AAG | GGA | CTG | CAG | TAT | GCG | GCC | CAG | GAG | GGG | CTA | TTG | 144 |
| Arg | Ile | Thr 35 | Asp | Lys | Gly | Leu | Gln 40 | Tyr | Ala | Ala | Gln | Glu 45 | Gly | Leu | Leu | |
| GCT | CTG | CAG | AGT | GAG | CTG | CTC | AGG | ATC | ACG | CTG | CCT | GAC | TTC | ACC | GGG | 192 |
| Ala | Leu 50 | Gln | Ser | Glu | Leu | Leu 55 | Arg | Ile | Thr | Leu | Pro 60 | Asp | Phe | Thr | Gly | |
| GAC | TTG | AGG | ATC | CCC | CAC | GTC | GGC | CGT | GGG | CGC | TAT | GAG | TTC | CAC | AGC | 240 |
| Asp 65 | Leu | Arg | Ile | Pro | His 70 | Val | Gly | Arg | Gly | Arg 75 | Tyr | Glu | Phe | His | Ser 80 | |
| CTG | AAC | ATC | CAC | AGC | TGT | GAG | CTG | CTT | CAC | TCT | GCG | CTG | AGG | CCT | GTC | 288 |
| Leu | Asn | Ile | His | Ser 85 | Cys | Glu | Leu | Leu | His 90 | Ser | Ala | Leu | Arg | Pro 95 | Val | |
| CCC | GGC | CAG | GGC | CTG | AGT | CTC | AGC | ATC | TCC | GAC | TCC | TCC | ATC | CGG | GTC | 336 |
| Pro | Gly | Gln | Gly 100 | Leu | Ser | Leu | Ser | Ile 105 | Ser | Asp | Ser | Ser | Ile 110 | Arg | Val | |
| CAG | GGC | AGG | TGG | AAG | GTG | CGC | AAG | TCA | TTC | TTC | AAA | CTA | CAG | GGC | TCC | 384 |
| Gln | Gly | Arg 115 | Trp | Lys | Val | Arg | Lys 120 | Ser | Phe | Phe | Lys | Leu 125 | Gln | Gly | Ser | |
| TTT | GAT | GTC | AGT | GTC | AAG | GGC | ATC | AGC | ATT | TCG | GTC | AAC | CTC | CTG | TTG | 432 |
| Phe | Asp | Val | Ser 130 | Val | Lys | Gly | Ile | Ser 135 | Ile | Ser | Val | Asn | Leu 140 | Leu | Leu | |

-continued

|  |  | 130 |  |  |  |  | 135 |  |  |  |  | 140 |  |  |  |  |
|---|---|---|---|---|---|---|---|---|---|---|---|---|---|---|---|---|
| GGC | AGC | GAG | TCC | TCC | GGG | AGG | CCC | ACA | GGT | TAC | TGC | CTC | AGC | TGC | AGC | 480 |
| Gly | Ser | Glu | Ser | Ser | Gly | Arg | Pro | Thr | Gly | Tyr | Cys | Leu | Ser | Cys | Ser |  |
| 145 |  |  |  |  | 150 |  |  |  |  | 155 |  |  |  |  | 160 |  |

| AGT | GAC | ATC | GCT | GAC | GTG | GAG | GTG | GAC | ATG | TCG | GGA | GAT | TCG | GGG | TGG | 528 |
|---|---|---|---|---|---|---|---|---|---|---|---|---|---|---|---|---|
| Ser | Asp | Ile | Ala | Asp | Val | Glu | Val | Asp | Met | Ser | Gly | Asp | Ser | Gly | Trp |  |
|  |  |  |  | 165 |  |  |  |  | 170 |  |  |  |  | 175 |  |  |

| CTC | TTG | AAC | CTC | TTC | CAC | AAC | CAG | ATT | GAG | TCC | AAG | TTC | CAG | AAA | GTA | 576 |
|---|---|---|---|---|---|---|---|---|---|---|---|---|---|---|---|---|
| Leu | Leu | Asn | Leu | Phe | His | Asn | Gln | Ile | Glu | Ser | Lys | Phe | Gln | Lys | Val |  |
|  |  |  | 180 |  |  |  |  | 185 |  |  |  |  | 190 |  |  |  |

| CTG | GAG | AGC | AGG | ATT | TGC | GAA | ATG | ATC | CAG | AAA | TCA | GTG | TCC | TCC | GAT | 624 |
|---|---|---|---|---|---|---|---|---|---|---|---|---|---|---|---|---|
| Leu | Glu | Ser | Arg | Ile | Cys | Glu | Met | Ile | Gln | Lys | Ser | Val | Ser | Ser | Asp |  |
|  |  | 195 |  |  |  |  | 200 |  |  |  |  | 205 |  |  |  |  |

| CTA | CAG | CCT | TAT | CTC | CAA | ACT | CTG | CCA | GTT | ACA | ACA | GAG | ATT | GAC | AGT | 672 |
|---|---|---|---|---|---|---|---|---|---|---|---|---|---|---|---|---|
| Leu | Gln | Pro | Tyr | Leu | Gln | Thr | Leu | Pro | Val | Thr | Thr | Glu | Ile | Asp | Ser |  |
| 210 |  |  |  |  | 215 |  |  |  |  | 220 |  |  |  |  |  |  |

| TTC | GCC | GAC | ATT | GAT | TAT | AGC | TTA | GTG | GAA | GCC | CCT | CGG | GCA | ACA | GCC | 720 |
|---|---|---|---|---|---|---|---|---|---|---|---|---|---|---|---|---|
| Phe | Ala | Asp | Ile | Asp | Tyr | Ser | Leu | Val | Glu | Ala | Pro | Arg | Ala | Thr | Ala |  |
| 225 |  |  |  |  | 230 |  |  |  |  | 235 |  |  |  |  | 240 |  |

| CAG | ATG | CTG | GAG | GTG | ATG | TTT | AAG | GGT | GAA | ATC | TTT | CAT | CGT | AAC | CAC | 768 |
|---|---|---|---|---|---|---|---|---|---|---|---|---|---|---|---|---|
| Gln | Met | Leu | Glu | Val | Met | Phe | Lys | Gly | Glu | Ile | Phe | His | Arg | Asn | His |  |
|  |  |  |  | 245 |  |  |  |  | 250 |  |  |  |  | 255 |  |  |

| CGT | TCT | CCA | GTT | ACC | CTC | CTT | GCT | GCA | GTC | ATG | AGC | CTT | CCT | GAG | GAA | 816 |
|---|---|---|---|---|---|---|---|---|---|---|---|---|---|---|---|---|
| Arg | Ser | Pro | Val | Thr | Leu | Leu | Ala | Ala | Val | Met | Ser | Leu | Pro | Glu | Glu |  |
|  |  |  | 260 |  |  |  |  | 265 |  |  |  |  | 270 |  |  |  |

| CAC | AAC | AAA | ATG | GTC | TAC | TTT | GCC | ATC | TCG | GAT | TAT | GTC | TTC | AAC | ACG | 864 |
|---|---|---|---|---|---|---|---|---|---|---|---|---|---|---|---|---|
| His | Asn | Lys | Met | Val | Tyr | Phe | Ala | Ile | Ser | Asp | Tyr | Val | Phe | Asn | Thr |  |
|  |  | 275 |  |  |  |  | 280 |  |  |  |  | 285 |  |  |  |  |

| GCC | AGC | CTG | GTT | TAT | CAT | GAG | GAA | GGA | TAT | CTG | AAC | TTC | TCC | ATC | ACA | 912 |
|---|---|---|---|---|---|---|---|---|---|---|---|---|---|---|---|---|
| Ala | Ser | Leu | Val | Tyr | His | Glu | Glu | Gly | Tyr | Leu | Asn | Phe | Ser | Ile | Thr |  |
| 290 |  |  |  |  | 295 |  |  |  |  | 300 |  |  |  |  |  |  |

| GAT | GAC | ATG | ATA | CCG | CCT | GAC | TCT | AAT | ATC | CGA | CTG | ACC | ACC | AAG | TCC | 960 |
|---|---|---|---|---|---|---|---|---|---|---|---|---|---|---|---|---|
| Asp | Asp | Met | Ile | Pro | Pro | Asp | Ser | Asn | Ile | Arg | Leu | Thr | Thr | Lys | Ser |  |
| 305 |  |  |  |  | 310 |  |  |  |  | 315 |  |  |  |  | 320 |  |

| TTC | CGA | CCC | TTC | GTC | CCA | CGG | TTA | GCC | AGG | CTC | TAC | CCC | AAC | ATG | AAC | 1008 |
|---|---|---|---|---|---|---|---|---|---|---|---|---|---|---|---|---|
| Phe | Arg | Pro | Phe | Val | Pro | Arg | Leu | Ala | Arg | Leu | Tyr | Pro | Asn | Met | Asn |  |
|  |  |  |  | 325 |  |  |  |  | 330 |  |  |  |  | 335 |  |  |

| CTG | GAA | CTC | CAG | GGA | TCA | GTG | CCC | TCT | GCT | CCG | CTC | CTG | AAC | TTC | AGC | 1056 |
|---|---|---|---|---|---|---|---|---|---|---|---|---|---|---|---|---|
| Leu | Glu | Leu | Gln | Gly | Ser | Val | Pro | Ser | Ala | Pro | Leu | Leu | Asn | Phe | Ser |  |
|  |  |  | 340 |  |  |  |  | 345 |  |  |  |  | 350 |  |  |  |

| CCT | GGG | AAT | CTG | TCT | GTG | GAC | CCC | TAT | ATG | GAG | ATA | GAT | GCC | TTT | GTG | 1104 |
|---|---|---|---|---|---|---|---|---|---|---|---|---|---|---|---|---|
| Pro | Gly | Asn | Leu | Ser | Val | Asp | Pro | Tyr | Met | Glu | Ile | Asp | Ala | Phe | Val |  |
|  |  | 355 |  |  |  |  | 360 |  |  |  |  | 365 |  |  |  |  |

| CTC | CTG | CCC | AGC | TCC | AGC | AAG | GAG | CCT | GTC | TTC | CGG | CTC | AGT | GTG | GCC | 1152 |
|---|---|---|---|---|---|---|---|---|---|---|---|---|---|---|---|---|
| Leu | Leu | Pro | Ser | Ser | Ser | Lys | Glu | Pro | Val | Phe | Arg | Leu | Ser | Val | Ala |  |
| 370 |  |  |  |  | 375 |  |  |  |  | 380 |  |  |  |  |  |  |

| ACT | AAT | GTG | TCC | GCC | ACC | TTG | ACC | TTC | AAT | ACC | AGC | AAG | ATC | ACT | GGG | 1200 |
|---|---|---|---|---|---|---|---|---|---|---|---|---|---|---|---|---|
| Thr | Asn | Val | Ser | Ala | Thr | Leu | Thr | Phe | Asn | Thr | Ser | Lys | Ile | Thr | Gly |  |
| 385 |  |  |  |  | 390 |  |  |  |  | 395 |  |  |  |  | 400 |  |

| TTC | CTG | AAG | CCA | GGA | AAG | GTA | AAA | GTG | GAA | CTG | AAA | GAA | TCC | AAA | GTT | 1248 |
|---|---|---|---|---|---|---|---|---|---|---|---|---|---|---|---|---|
| Phe | Leu | Lys | Pro | Gly | Lys | Val | Lys | Val | Glu | Leu | Lys | Glu | Ser | Lys | Val |  |
|  |  |  |  | 405 |  |  |  |  | 410 |  |  |  |  | 415 |  |  |

| GGA | CTA | TTC | AAT | GCA | GAG | CTG | TTG | GAA | GCG | CTC | CTC | AAC | TAT | TAC | ATC | 1296 |
|---|---|---|---|---|---|---|---|---|---|---|---|---|---|---|---|---|
| Gly | Leu | Phe | Asn | Ala | Glu | Leu | Leu | Glu | Ala | Leu | Leu | Asn | Tyr | Tyr | Ile |  |
|  |  |  | 420 |  |  |  |  | 425 |  |  |  |  | 430 |  |  |  |

| CTT | AAC | ACC | CTC | TAC | CCC | AAG | TTC | AAT | GAT | AAG | TTG | GCC | GAA | GGC | TTC | 1344 |
|---|---|---|---|---|---|---|---|---|---|---|---|---|---|---|---|---|
| Leu | Asn | Thr | Leu | Tyr | Pro | Lys | Phe | Asn | Asp | Lys | Leu | Ala | Glu | Gly | Phe |  |
|  |  | 435 |  |  |  |  | 440 |  |  |  |  | 445 |  |  |  |  |

| CCC | CTT | CCT | CTG | CTG | AAG | CGT | GTT | CAG | CTC | TAC | GAC | CTT | GGG | CTG | CAG | 1392 |
|---|---|---|---|---|---|---|---|---|---|---|---|---|---|---|---|---|
| Pro | Leu | Pro | Leu | Leu | Lys | Arg | Val | Gln | Leu | Tyr | Asp | Leu | Gly | Leu | Gln |  |

```
                    450                        455                        460
ATC  CAT  AAG  GAC  TTC  CTG  TTC  TTG  GGT  GCC  AAT  GTC  CAA  TAC  ATG  AGA     1440
Ile  His  Lys  Asp  Phe  Leu  Phe  Leu  Gly  Ala  Asn  Val  Gln  Tyr  Met  Arg
465                 470                      475                       480

GTT  TGAGGACAAG  AAAGATGAAG  CTTGGAGGTC  ACAGGCTGGA  TCTGCTTGTT              1493
Val

GCATTTCCAG  CTGTGCAGCA  CGTCTCAGAG  ATTCTTGAAG  AATGAAGACA  TTTCTGCTCT        1553

CAGCTCCGGG  GGTGAGGTGT  GCCTGGCCTC  TGCCTCCACC  CTCCTCCTCT  TCACCAGGTG        1613

CATGCATGCC  CTCTCTGAGT  CTGGACTTTG  CTTCCCCTCC  AGGAGGGACC  ACCCTCCCCG        1673

ACTGGCCTGG  GATATCTTTA  CAAGCAGGCA  CTGTATTTTT  TTATTCGCCA  TCTGATCCCC        1733

ATGCCTAGCA  GAGTGCTGGC  ACTTAGTAGG  TCCTCAATAA  ATATTTAGGT  CGACGAGCTC        1793

GAGAATTC                                                                    1801
```

(2) INFORMATION FOR SEQ ID NO:9:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO:9:

```
Met  Gly  Ala  Leu  Ala  Arg  Ala  Leu  Pro  Ser  Ile  Leu  Leu  Ala  Leu  Leu
 1                  5                       10                      15

Leu  Thr  Ser  Thr  Pro  Glu  Ala  Leu  Gly  Ala  Asn  Pro  Gly  Leu  Val  Ala
                20                       25                  30

Arg  Ile  Thr  Asp  Lys  Gly  Leu  Gln  Tyr  Ala  Ala  Gln  Glu  Gly  Leu  Leu
           35                       40                       45

Ala  Leu  Gln  Ser  Glu  Leu  Leu  Arg  Ile  Thr  Leu  Pro  Asp  Phe  Thr  Gly
      50                       55                       60

Asp  Leu  Arg  Ile  Pro  His  Val  Gly  Arg  Gly  Arg  Tyr  Glu  Phe  His  Ser
 65                      70                       75                       80

Leu  Asn  Ile  His  Ser  Cys  Glu  Leu  Leu  His  Ser  Ala  Leu  Arg  Pro  Val
                     85                       90                       95

Pro  Gly  Gln  Gly  Leu  Ser  Leu  Ser  Ile  Ser  Asp  Ser  Ser  Ile  Arg  Val
                100                      105                      110

Gln  Gly  Arg  Trp  Lys  Val  Arg  Lys  Ser  Phe  Phe  Lys  Leu  Gln  Gly  Ser
           115                      120                      125

Phe  Asp  Val  Ser  Val  Lys  Gly  Ile  Ser  Ile  Ser  Val  Asn  Leu  Leu  Leu
     130                      135                      140

Gly  Ser  Glu  Ser  Ser  Gly  Arg  Pro  Thr  Gly  Tyr  Cys  Leu  Ser  Cys  Ser
145                      150                      155                      160

Ser  Asp  Ile  Ala  Asp  Val  Glu  Val  Asp  Met  Ser  Gly  Asp  Ser  Gly  Trp
                     165                      170                      175

Leu  Leu  Asn  Leu  Phe  His  Asn  Gln  Ile  Glu  Ser  Lys  Phe  Gln  Lys  Val
                180                      185                      190

Leu  Glu  Ser  Arg  Ile  Cys  Glu  Met  Ile  Gln  Lys  Ser  Val  Ser  Ser  Asp
           195                      200                      205

Leu  Gln  Pro  Tyr  Leu  Gln  Thr  Leu  Pro  Val  Thr  Thr  Glu  Ile  Asp  Ser
     210                      215                      220

Phe  Ala  Asp  Ile  Asp  Tyr  Ser  Leu  Val  Glu  Ala  Pro  Arg  Ala  Thr  Ala
225                      230                      235                      240

Gln  Met  Leu  Glu  Val  Met  Phe  Lys  Gly  Glu  Ile  Phe  His  Arg  Asn  His
                     245                      250                      255
```

| | | | | | | | | | | | | | | |
|---|---|---|---|---|---|---|---|---|---|---|---|---|---|---|
| Arg | Ser | Pro | Val 260 | Thr | Leu | Leu | Ala | Ala 265 | Val | Met | Ser | Leu | Pro 270 | Glu | Glu |
| His | Asn | Lys 275 | Met | Val | Tyr | Phe | Ala 280 | Ile | Ser | Asp | Tyr | Val 285 | Phe | Asn | Thr |
| Ala | Ser 290 | Leu | Val | Tyr | His | Glu 295 | Glu | Gly | Tyr | Leu | Asn 300 | Phe | Ser | Ile | Thr |
| Asp 305 | Asp | Met | Ile | Pro | Pro 310 | Asp | Ser | Asn | Ile | Arg 315 | Leu | Thr | Thr | Lys | Ser 320 |
| Phe | Arg | Pro | Phe | Val 325 | Pro | Arg | Leu | Ala | Arg 330 | Leu | Tyr | Pro | Asn | Met 335 | Asn |
| Leu | Glu | Leu | Gln 340 | Gly | Ser | Val | Pro | Ser 345 | Ala | Pro | Leu | Leu | Asn 350 | Phe | Ser |
| Pro | Gly | Asn 355 | Leu | Ser | Val | Asp | Pro 360 | Tyr | Met | Glu | Ile | Asp 365 | Ala | Phe | Val |
| Leu | Leu 370 | Pro | Ser | Ser | Ser | Lys 375 | Glu | Pro | Val | Phe | Arg 380 | Leu | Ser | Val | Ala |
| Thr 385 | Asn | Val | Ser | Ala | Thr 390 | Leu | Thr | Phe | Asn | Thr 395 | Ser | Lys | Ile | Thr | Gly 400 |
| Phe | Leu | Lys | Pro | Gly 405 | Lys | Val | Lys | Val | Glu 410 | Leu | Lys | Glu | Ser | Lys 415 | Val |
| Gly | Leu | Phe | Asn 420 | Ala | Glu | Leu | Leu | Glu 425 | Ala | Leu | Leu | Asn | Tyr 430 | Tyr | Ile |
| Leu | Asn | Thr 435 | Leu | Tyr | Pro | Lys | Phe 440 | Asn | Asp | Lys | Leu | Ala 445 | Glu | Gly | Phe |
| Pro | Leu 450 | Pro | Leu | Leu | Lys | Arg 455 | Val | Gln | Leu | Tyr | Asp 460 | Leu | Gly | Leu | Gln |
| Ile 465 | His | Lys | Asp | Phe | Leu 470 | Phe | Leu | Gly | Ala | Asn 475 | Val | Gln | Tyr | Met | Arg 480 |
| Val | | | | | | | | | | | | | | | |